(12) United States Patent
Bihain et al.

(10) Patent No.: US 7,220,722 B2
(45) Date of Patent: *May 22, 2007

(54) LIPOPROTEIN-REGULATING MEDICANTS

(75) Inventors: Bernard Bihain, Cancale (FR); Lydie Bougueleret, Petit Lancy (CH); Frances Yen-Potin, San Diego, CA (US)

(73) Assignee: Serono Genetics Institute S.A., Evry (FR)

( * ) Notice: Subject to any disclaimer, the term of this patent is extended or adjusted under 35 U.S.C. 154(b) by 257 days.

This patent is subject to a terminal disclaimer.

(21) Appl. No.: 10/072,159

(22) Filed: Feb. 5, 2002

(65) Prior Publication Data

US 2002/0151498 A1  Oct. 17, 2002

Related U.S. Application Data

(62) Division of application No. 09/485,316, filed as application No. PCT/IB98/01256 on Aug. 6, 1998, now Pat. No. 6,344,441.

(30) Foreign Application Priority Data

Aug. 6, 1997 (FR) .................................. 97 10088
Apr. 22, 1998 (FR) .................................. 98 05032

(51) Int. Cl.
*A61K 38/00* (2006.01)

(52) U.S. Cl. ........................ 514/12; 424/422; 530/350; 530/399

(58) Field of Classification Search ............. 514/2; 530/350

See application file for complete search history.

(56) References Cited

U.S. PATENT DOCUMENTS

| | | |
|---|---|---|
| 6,344,441 B1 | 2/2002 | Bihain et al. |
| 6,566,332 B2 | 5/2003 | Fruebis et al. |
| 6,579,852 B2 | 6/2003 | Fruebis et al. |
| 6,635,431 B1 | 10/2003 | Bihain et al. |
| 6,867,189 B2 | 3/2005 | Lucas et al. |
| 6,946,444 B2 | 9/2005 | Bihain et al. |
| 6,967,091 B2 | 11/2005 | Fruebis et al. |
| 2003/0100500 A1 | 5/2003 | Fruebis et al. |
| 2003/0215836 A1 | 11/2003 | Young et al. |
| 2003/0224501 A1 | 12/2003 | Young et al. |
| 2004/0067881 A1 | 4/2004 | Fruebis et al. |
| 2004/0077051 A1 | 4/2004 | Bihain et al. |
| 2005/0003997 A1 | 1/2005 | Lucas et al. |
| 2005/0054565 A1 | 3/2005 | Lucas et al. |
| 2005/0069971 A1 | 3/2005 | Lucas et al. |

FOREIGN PATENT DOCUMENTS

| | | |
|---|---|---|
| EP | 1033134 A1 | 9/2000 |
| WO | WO 96/30400 A1 | 10/1996 |
| WO | WO 96/34981 A2 | 11/1996 |
| WO | WO 96/39429 A2 | 12/1996 |
| WO | WO 97/27286 A1 | 7/1997 |
| WO | WO98/01257 A2 | 1/1998 |
| WO | WO 98/20165 A2 | 5/1998 |
| WO | WO 98/54311 A1 | 12/1998 |
| WO | WO 99/04000 A1 | 1/1999 |
| WO | WO 99/07736 A2 | 2/1999 |
| WO | WO 99/10492 A1 | 3/1999 |

OTHER PUBLICATIONS

Fasshauer et al. (2004), Adiponectin, obesity, and cardiovascular disease, Biochimie 86(11): 779-784.*
Gil-Campos et al. (2004), Adiponectin, the missing link in insulin resistance and obesity, Clin. Nutr. 23(5): 963-974.*
Bays (2004), Current and investigational antiobesity agents and obesity therapeutic treatment targets, Obes. Res. 12(8): 1197-1211.*
Hu et al. (1996), AdipoQ is a Novel Adipose-specific Gene Dysregulated in Obesity, J. Biol. Chem. 271(18): 10697-10703.*
Maeda et al. (1996), cDNA Cloning and Expression of a Novel Adipose Specific Collagen-like Factor, apM1 (Adipose Most Abundant Gene Transcript 1), Biochem. Biophys. Res. Comm. 221: 286-289.*
Scherer et al. (1995), A Novel Serum Protein Similar to C1q, Produced Exclusively in Adipocytes, J. Biol. Chem. 270(45): 26746-26749.*
Bowie et al., Science 247: 1306-1310, 1990.*
Wells, Biochemistry 29:8509-8517, 1990.*
Alexeev and Yoon, "Stable and Inheritable Changes in Genotype and Phenotype of Albino Melanocytes Induced by an RNA-DNA Oligonucleotide"; Nature Biotech., 16:1343-1346, 1998.
Arita, et al., "Paradoxical Decrease of an Adipose-Specific Protein, Adiponectin, in Obesity", Biochem. and Biophys. Research Comm. 257:79-83, 1999 (Academic Press).
Costal, P., et al., "Peroxisome Proliferator-Activated Receptor a-Isoform Deficiency Leads to Progressive Dyslipidemia With Sexually Dimorphic Obesity and Steatosis", J. Biol. Chem., vol. 273, No. 45, 29577-29585, Nov. 6, 1998 (The American Society for Biochemistry and Molecular Biology, Inc.).
Imagawa, et al., "Structure-Function Studies of Human Leptin", J. Biol. Chem., vol. 273, No. 52:35245-35249, Dec. 25, 1998 (The American Society for Biochemistry and Molecular Biology, Inc.).
Kersten, S., et al., "Peroxisome Proliferator?Activated Receptor aMEOIATES the Adaptive Response to Fasting", J. Clin. Invest, vol. 103, No. 11:1489-1498, Jun. 1999 (The American Society for Clinical Investigations).
Groenen, et al, "Structure, sequence and chromosome 19 localization of human USF2 and its rearrangement in a pateint with multicystic renal adysplasia",Genomics 38:141-148 (1995), XP002067467.

(Continued)

Primary Examiner—Eileen O'Hara
Assistant Examiner—Gyan Chandra
(74) Attorney, Agent, or Firm—Saliwanchik, Lloyd & Saliwanchik

(57) ABSTRACT

Methods and pharmaceutical compositions useful for treating obesity-related disorders using ApM-1 and related proteins.

19 Claims, 7 Drawing Sheets

OTHER PUBLICATIONS

Saito, et al., "Organization of the Gene for Gelatin-Binding Protein (GBP28)", Gene, 229:67-73, Jan. 12, 1999 (Elsevier Science B.V.).

Schaffler, et al., "The Human apM-1, An Adipocyte-Specific Gene Linked to the Family of TNF'S and to Genes Expressed in Activated T Cells, is Mapped to Chromosone 1q21.3-q23, A Susceptibility Locus Identified for Familia Combined Hyperlipidaemia (FCH)", Biochem. and Biophys. Res. Comm. 260:416-425, May 7, 1999 (Academic Press).

Shimomura, et al., "Leptin Reverses Insulin Resistance and Diabetes Mellitus in Mice With Congenital Lipodystrophy", Nature, 401:73-76, Sep. 2, 1999.

Uotani, S., "Functional Properties of Leptin Receptor Isoforms Internalization and Edgradation of Leptin and Legand-Induced Receptor Downregulation Diabetes", 48:279-286, Feb. 1999.

Vansant, G., et al., "Determinants of Postprandial Lipernia in Obese Women", Intl. Jr. of Obesity, 23:Supp. 1, 14-21, 1999 (Stockton Press).

Yen, et al., "Molecular Cloning of a Lipolysis-Stimulated Remnant Receptor Expressed in the Liver", J. Biol. Chem., vol. 274, #19:13390-13398, 1999 (The American Society for Biochemistry and Molecular Biology, Inc.).

Barsh, G., et al., "Genetics of Body-Weight Regulation", Nature, vol. 404:644-651, Apr. 6, 2000.

Friedman, J.M., "Obesity in the New Millennium", Nature, vol. 404:632-634, Apr. 6, 2000 (Macmilan Magazines Ltd.).

Oksana, G., et al., "Hormones: Leptin and Diabetes in Lipoatrophic Mice", Nature, vol. 403:850, Feb. 24, 2000 (Macmillan Publishers Ltd.).

Oksana, G., et al., "Lack of Responses to a [(Beta).Sub.3]-Adrenergic Agonist in Lipoatrophic A-Zip Mice", Diabetes, vol. 49, #11:1910, Nov. 2000 (American Diabetes Association).

Hotta, K., et al., "Plasma Concentrations FO a Novel, Adipose-Specific Protein, Adiponectin, in Type 2 Diabetic Patients", Arteriosclar Thromb Vasc Biol., 1595-1599, Jun. 2000 (American Heart Association, Inc.).

Kishore, U., et al., "Modular Organization of Proteins Containing Clq-like Globular Domain", Immunopharmacology 42 (1999) 15-21 (1999 Elsevier Science B.V.).

Kishor, U., et al., "Clq: Structure, Function, and Receptors", Immunopharmacology 49(2000) 159-170 (2000) Elsevier Science B.V.).

Kopelman, P., "Obesity as a Medical Problem", Nature, vol. 404:635-643, Apr. 6, 2000 (Macmillan Magazines Ltd.).

Mann, C., et al., "Inhibitory Effects of Specific Apolipoprotein C-III Isoforms on the Binding of Triglyceride-Rich Lipoproteins to the Lipolysis-Stimulated Receptor", The Journal of Biological Chemistry, vol. 272, #50:31348-31354, 1997 (The American Society for Biochemistry and Molecular Biology, Inc.).

Nakano, Y., et al., "Isolation and Characterization of GBP28, A Novel Gelatin-Binding Purified From Human Plasma", J. Biochem, vol. 120, #4:803-812 (1996).

Okamoto, Y., et al., "An Adipocyte-Derived Plasma Protein, Adiponectin, Adheres to Injured Vascular Walls", Horm Metab Res 2000; 32:47-50 (Georg Thieme Verlag Stuttgart-New York).

Ouchi, N., et al., "Novel Modulator for Endothelial Adhesion Molecules / Adipocyte-Derived Plasma Protein Adiponectin", Circulation, vol. 100:2473-2476, Dec. 21/28, 1999 (American Heart Association).

Saito, K., et al., "Regulation of Gelatin-Binding Protein 28 (G8P28) Gene Expression by C/EBP", Biol. Pharm. Bull. 22(11) 1158-1162 (1999).

Shapiro, L., et al., "The Crystal Structure of a Complement-1q Family Protein Suggests an Evolutionary Link to Tumor Necrosis Factor", Current Biology, vol. 8, No. 6, pp. 335-338.

Takehashi, M., et al., "Genomic Structure and Mutations in Adipose-Specific Gene, Adiponectin", International Journal of Obesity (2000) 24, 861-868 (Macmillan Publishers Ltd.).

Yokota, T., et al., "Adiponectin, a New Member of the Family of Soluble Defense Collagens, Negatively Regulates the Growth of Myelomonocytic Progenitors and the Functions of Macrophages", Blood, Sep. 1, 2000—vol. 96, No. 5, pp. 1723-1732 (The American Society of Hematology).

Bihain, B., et al., "The Lipolysis-Stimulated Receptor: A Gene at Last", Current Opinion in Lipodology, vol. 9, No. 3, pp. 221-224, Jun. 1998.

Bihain, B.E., et al.; "Characterization and purification of the lipolysis-stimulated receptor," Elsevier Science B.V., pp. 465-470 (1995).

Ghebrehiwet, et al., "Isolation, cDNA Cloning, and Overexpression of a 33-kD Cell Surface Glycoprotein that Binds to the Globular "Heads" of Clq"; J. Exp. Med., 179:1809-1821 (1994).

Hayward, et al.; "The cDNA Sequence of Human Endothelial Cell Multimerin"; J. Biol. Chem., 290:18246-18251 (1995).

Henrion, et al.; "Structure, Sequence, and Chromosomal Location of the Gene for USF2 Transcription Factors in Mouse", Genomics, 25:36-43 (1995).

Hu, et al.; "AdipoQ is a Novel Adipose-specific Gene Dysregulated in Obesity"; J. Biol. Chem., 271:10697-10703 (1996).

Maeda, et al.; "cDNA Cloning and expression of a novel adipose specific collagen-like factor, apM1 (Adipose most abundant gene transcript 1)"; Biochem. and Biophys. Research Comm., 221:286-289 (1996).

Sellar, et al.; "Characterization and organization of the genes encoding the A-, B- and C-chains of human complement subcomponent Clq"; Biochemical Journal, 274:418-190 (1991).

Troussard, A.A., et al.; "Inhibitory effect on the lipolysis-stimulated receptor of the 39-kDa receptor-associated protein"; Jr. of Biol. Chem.; 270:17068-71 (1995).

Urade, Y., et al.; "Precerebellin is a cerebellum-specific protein with similarity to the globular domain of complement Clq B chain"; Proc. Natl. Sci. USA; 88:1069-1073 (1991).

Das, K., et al.; "Chromosomal localizations, expression pattern, and promoter analysis of the mouse gene encoding adipocyte-specific secretory protein ACRP30"; Biochemical and Biophysical Research Communications, 2001, 280:1120-1129; Academic Press [available online at http://www.idealibrary.com].

Nakano, Y., et al.; "Isolation and Characterization of GBP28, a Novel Gelstin-Binding Protein Purified from Human Plasma"; J. Biochem., 1996, 120(4):803-812.

Austin, et al. "Hypertriglyceridemia as a Cardiovascular Risk Factor," *Am. J. Cardiol.* (1998), vol. 81, pp. 7B-12B.

Baldo, et al. "The Adipsin-Acylation Stimulating Protein System and Regulation of Intracellular Triglyceride Synthesis," *J. Clin. Invest.* (1993), vol. 92, pp. 1543-1547.

Bartles, J.R. et al. "Biogenesis of the Rate Hepatocyte Plasma Membrane," *Methods Enzymol.* (1990), vol. 191, pp. 825-841.

Bihain, et al. "Free Fatty Acids Activate a High Affinity Saturable Pathway for Degradation of Low-Density Lipoproteins in Fibroblasts from a Subject Homozygous for Familial Hypercholesterolemia," *Biochemistry* (1992), vol. 31, No. 19, pp. 4628-4636.

Brendel, V. et al. "Methods and algorithms for statistical analysis of protein sequences," *Proc. Natl. Acad. Sci. USA* (1992), vol. 89, pp. 2002-2006.

Chen, W.J. et al. "NPXY, a sequence often found in cytoplasmic tails, is required for coated pit-mediated internalization of the low density lipoprotein receptor," *J. Biol. Chem.* (1990), vol. 265, pp. 3116-3123.

Cole-Strauss et al. "Correction of the Mutation Responsible for Sickle Cell Anemia by an RNA-DNA Oligonucleotide," *Science* (1996), vol. 273, pp. 1386-1389.

Davis, C.G. et al. "The J.D. Mutation in Familial Hypercholesterolemia: Amino Acid Substitution in Cytoplasmic Domain Impedes Internalization of LDL Receptors," *Cell* (1986), vol. 45, pp. 15-24.

Dietrich, J. et al. "CD3$\gamma$ Contains a Phosphoserine-Dependent Di-Leucine Motif Involved in Down-Regulation of the T Cell Receptor," *EMBO Journal* (1994), vol. 13, pp. 2156-2166.

Everhart, J.E. "Weight Change and Obesity After Liver Transplantation: Incidence and Risk Factors," *Liver Transpl. Surg.* (1998), vol. 4, pp. 285-296.

Feeman, JR., W.E. "Hypertriglyceridemia and Atherosclerosis," *Annals of Internal Med.* (1998), vol. 128, No. 1, pp. 73-74.

Goldstein, J.L., et al. "Familial Hypercholesterolemia," in *The Metabolic and Molecular Bases of Inherited Disease* (vol. II, 7th ed., Scriver, C.R., Beaudet, A.L., Sly, W.S., Valle, B. editors, 1995), pp. 1981-2030; McGraw-Hill; New York, New York, USA.

Goldstein, et al. "Hyperlipidemia in Coronary Heart Disease," *J. Clin. Invest.* (1973), vol. 52, pp. 1533-1543.

Gura, et al. "Obesity Sheds Its Secrets," *Science* (1997), vol. 275, pp. 751-753.

Herz, J., et al. "Surface Location and High Affinity for Calcium of a 500-kd liver Membrane Protein Closely Related to the LDL-receptor Suggest a Physiological Role as Lipoprotein Receptor," *European Molecular Biology Laboratory* (1988), vol. 7, pp. 4119-4127.

Honore, B., et al. "Cloning and Expression of a cDNA Covering the Complete Coding Region of the P32 subunit of Human pre-mRNA Splicing Factor SF2," *Gene* (1993), vol. 134, pp. 283-287.

Hu, E., et al. "AdipoQ is a Novel Adipose-specific Gene Dysregulated in Obesity," *J. Biol. Chem.* (1996), vol. 271, No. 18, pp. 10697-10703.

Huettinger, M., et al. "Charecteristics of Chlylomicron Remnant Uptake into Rat Liver," *Clin. Biochem.* (1988), vol. 21, pp. 87-92.

Karpe, F., et al. "Clearance of Lipoprotein Remnant Particles in Adipose Tissue and Muscle in Humans," *J. Lipid, Res.* (1997), vol. 38, pp. 2335-2343.

Karpe, F., et al. "Magnitude of Alimentary Lipemia is Related to Intima-media Thickness of the Common Carotid Artery in Middle-aged Men," *Elsevier Science Ireland* (1998), vol. 141, pp. 307-314.

Khallou, et al. "Correction of delayed postprandial plasma lipid response in genetically obese mice by injection of recombinant leptin": Abstract from the 69th Scientific Sessions, New Orleans, L.A: Supplemental to Circulation, American Hear Assoc., (1996), vol. 94:8.

Krainer, A.R., et al. "Functional Expression of Cloned Human Splicing Factor SF2: Homology to RNA-Binding Proteins, U1 70K, and Drosophila Splicing Regulators," *Cell* (1991), vol. 66, pp. 383-394.

Lee, M. G-S., et al. "Characterization of a cDNA Encoding a Cysteine-Rich Cell Surface Protein Located in the Flagellar Pocket of the Protozoan *Trypanosoma brucei,*" *Molec. Cell. Biol.* (1990), vol. 10, pp. 4506-4517.

Letourneur, F., et al. "A Novel Di-Leucine Motif and a Tyrosine-Based Motif Independently Mediate Lysosomal Targeting and Endocytosis of CD3 Chains," *Cell* (1992), vol. 69, pp. 1143-1157.

Lewis, G.F., et al. "Postprandial Lipoprotein Metabolism in Normal and Obese Subjects: Comparison after the Vitamin A Fat-Loading Test," *J. of Clinic. Endo.* (1990), vol. 71, pp. 1041-1050.

Lin, et al. "Archaic Structure of the Gene Encoding Transcription Factor USF," *Journal of Biological Chemistry* (1994), vol. 269, No. 19, pp. 23894-28903.

Liu, Q., et al. "Design of Polydactyl Zinc-finger Proteins for Unique Addressing within Complex Genomes," *Proc. Natl. Acad. Sci. USA* (1997), vol. 94, pp. 5525-5530.

Mahley, R.W., et al. "Type III Hyperlipoproteinemia (Dysbetalipoproteinemia): The Role of Apolipoprotein E in Normal and Abnormal Lipoprotein Metabolism," in *The Molecular Basis of Inherited Disease* (1995), pp. 1953-1980; Scriver CR, Beaudet, A.L., Sly, W.S., Valle, D., editors; McGraw-Hill; New York.

Mann, et al. "Mechanism of Activation and Functional Significance of the Lipolysis-Stimulated Receptor. Evidence for Role as Chylomiscron Remnant Receptor," *Biochemistry* (1995), vol. 34, No. 33, pp. 10421-10431.

Massie, et al. "Inducible Overexpression of a Toxic Protein by an Andenovirus Vector with a Tetracycline-Regulatable Expression Cassette," *Journal of Virology* (1998), vol. 72, pp. 2289-2296.

Montague, et al. "Congenial Leptin Deficiency is Associated with Severe Early-onset Obesity in Humans," *Nature* (1997), vol. 387, pp. 903-908.

Parra-Lopez, C.A., et al. "Presentation on Class II MHC Molecules of Endogenous Lysozyme Targeted to the Endocytic Pathway," *J. Immunol.* (1997), vol. 158, pp. 2670-2679.

Pengue, G., et al. "Repression of Transcriptional Activity at a Distance by the Evolutionary Conserved KRAB Domain Present in a Subfamily of Zinc Finger Proteins," *Nucleic Acids Research* (1994), vol. 22, No. 15, pp. 2908-2914.

Rajput-Williams,J., et al. "Variation of Apolipoprotein-B Gene is Associated with Obesity, High Blood Cholesterol Levels, and Increased Risk of Coronary Heart Disease," *The Lancet* (1988), pp. 1442-1446.

Rutherford, S., et al. "Association of a Low Density Lipoprotein Receptor Micro-satellite Variant with Obesity," *Intl. J. of Obesity* (1997), vol. 21, pp. 1032-1037.

Schaffler, et al. "Identification and Characterization of the Human Adipocyte apM-1 Promoter," *Biochem. and Biophys. Res. Comm.* (1998), vol. 1399, pp. 187-189.

Scherer, et al. "A novel Serum Protein Similar to C1q, Produced Exclusively in Adipocytes," *J. Biol Chem.* (1995), vol. 270, pp. 26746-26749.

Shimabukuro, M., et al. "Direct Antidiabetic Effect of Leptin Through Triglyceride Depletion of Tissues," *Proc. Natl. Acad. Sci. USA* (1997), vol. 94, pp. 4637-4641.

Shimano, H., et al. "Overproduction of Cholesterol and Fatty Acids Causes Massive-Liver Enlargement in Transgenic Mice Expression Truncated SREBP-1a," *J. Clin. Invest.* (1996), vol. 98, pp. 1575-1584.

Shin, J., et al. "Phosphorylation-dependent Down-modulation of CD4 Requires a Specific Structure within the Cytoplasmic Domain of CD4," *J. of Biol. Chem.* (1991), vol. 266, pp. 10658-10665.

Simos, G., et al. "The lamin B Receptor-associated Protein p34 Shares Sequence Homology and Antigenetic Determinants with the Splicing Factor 2-associated with Protein p32," *FEBS Letters* (1994), vol. 346, pp. 225-228.

Steingrimsson, et al. "Murine Chromosomal Location of Five BHLH-Zip Transaction Factor Genes," *Genomics* (1995), vol. 28, pp. 179-183.

Van Den Berg, R.H., et al. "Intracellular Localization of the Human Receptor for the Globular Domains of C1q," *American Association of Immunologists* (1997), vol. 158, pp. 3909-3916.

Verhey, K.J., et al. "A Leu-Leu Sequence is Essential for COOH-terminal Targeting Signal of GLUT4 Glucose Transporter in Fibro-blasts," *J. Biol. Chem.* (1994), vol. 269, pp. 2353-2356.

Wang, et al. "Upstream Stimulatory Factor Binding to the E-box at -65 is required for Insulin Regulation of the Fatty Acid Synthase Promoter," *J. Biol. Chem.* (1997), vol. 272, pp. 26367-26374.

Yen, et al. "Identification of a Lipolysis-Stimulated Receptor That is Distinct from the LDL Receptor and the LDL Receptor Related Protein," *Biochemistry* (1994), vol. 33, No. 5, pp. 1172-1180.

Zhang, M., et al. "Tumor Necrosis Factor," in *The Cytokine Handbook* (3rd ed., 1998), pp. 517-548.

Zhong, G., et al. "Related Leucine-based Cytoplasmic Targeting Signals in Invariant Chain and Major Histocompatibility Complex Class II Molecules Control Endocytic Presentation of Distinct Determinants in a Single Protein," *J. Exp. Med.* (1997), vol. 185, pp. 429-438.

Groenen, P. et al., "Structure, Sequence and Chromosome 19 Location of Human USF2 . . . ", EMBL Sequence Database, Jan. 24, 1997, XP002067467.

Lamerdin, J.E., *Homo sapiens* DNA From Chromosome 19-COSMID R30879 Containing USF2, Genomic Sequence, EMBL Sequence Database, Mar. 26, 1997, XP002096567.

Lamerdin, J.E., et al., "Sequence Analysis of a 1 MB Region of Human 19Q13.1", EMBL Sequence Database, May 28, 1997, XP002096568.

Lamerdin, J.E., et al. "Human LISCH7", EMBL Sequence Database, Jul. 1, 1997, XP002096569.

Lamerdin, J.E., et al. "Liver-Specific BHLP-ZIP Transcritption Factor, LISCH7", EMBL Sequence Database, Jul. 1, 1997, XP002096570.

Lin, Q., et al., "LISCH7, A Liver Specific Gene Immediately Upstream of the USF2 Gene on Chromosome 7", EMBL Sequence Database, May 20, 1996, XP002096565.

Lin, Q., et al., "Liver-Specific Protein LISCH7", EMBL Sequence Database, Nov. 1, 1996, XP002096566.

U.S. Appl. No. 11/132,814, filed May 19, 2005, claims only.

Database Entrez Nucleotides, Accession No. BAA08227, a novel adipose specific collagen-like factor, Feb. 10, 1999.

Database Entrez Nucleotides, Accession No. D45371, Human apM1 mRNA, Feb. 10, 1999.

Online Mendelian Inheritance in Man database; Adipocyte, C1Q, and Collagen Domain Containing; ACDC; accessed Aug. 24, 2005.

Bloomgarden, Z. T. "Obesity, Hypertension, and Insulin Resistance" *Diabetes Care,* Nov. 2002, pp. 2088-2097, vol. 25, No. 11.

Steinberger, J. et al. "Obesity, Insulin Resistance, Diabetes, and Cardiovascular Risk in Children" *Circulation,* 2003, vol. 107, pp. 1448-1453.

De Jongh, R. T. et al. "Impaired Microvascular Function in Obesity" *Circulation,* 2004, pp. 2529-2535, vol. 109.

Ghebrehiwet, B. "Production and Characterization of a Murine Monoclonal IgM Antibody to Human C1q Receptor (C1qR)" *The Journal of Immunology,* Jul. 15, 1986, pp. 618-624, vol. 137, No. 2.

Ghebrehiwet, B. et al. "Isolation, cDNA Cloning, and Overexpression of a 33-kD Cell Surface Glycoprotein that Binds to the Globular "Heads" of C1q" *The Journal of Experimental Medicine,* Jun. 1994, pp. 1809-1821, vol. 179.

Joseph, K. et al. "Identification of the Zinc-dependent Endothelial Cell Binding Protein for High Molecular Weight Kininogen and Factor XII: Identify with the Receptor that Binds to the Globular "Heads" of C1q (gC1q-R)" *Proceedings of the National Academy of Sciences of the United States of America,* Aug. 1996, pp. 8552-8557, vol. 93.

\* cited by examiner

```
c1qa-117    FSAIRRNPPMG------GNVVIFDTVITNQEEPYQNHSGRFVCTVPGYYYFTFQVLSQW-
c1qb-122    FSATRTINVPLR----RDQTIRFDHVITNMNNNYEPRSGKFTCKVPGLYYFTYHASSRG-
c1qc-121    FTVTRQTHQPPA----PNSLIRFNAVLTNPQGDYDTSTGKFTCKVPGLYYFVYHASHTA-
mul-1160    FFASHTYGMTIP------GPILFNNLDVNYGASYTPRTGKFRIPYLGVYVFKYTIESFSA
cer-64      FSAIRSTNHEPSEMSNRTMIIYFDQVLVNIGNNFDSERSTFIAPRKGIYSFNFHVVKVYN
apm1-115    FSVGLETYVTI-----PNMPIRFTKIFYNQQNHYDGSTGKFHCNIPGLYYFAYHITVYMK
adQ-118     FSVGLETRVTV-----PNVPIRFTKIFYNQQNHYDNSTGKFYCNIPGLYYFSYHITVYMK
acrp-118    FSVGLETRVTV-----PNVPIRFTKIFYNQQNHYDGSTGKFYCNIPGLYYFSYHITVYMK
             *              *  *     .     *         *    * * *.

v              v
c1qa-117    --EICLSIVSSSRGQVRRSLGFCD---TTNKGLFQVVSGGMVLQLQQGDQVWVEKDPKKG
c1qb-122    --NLCVNLMRGRE-RAQKVVTFCD---YAYN-TFQVTTGGMVLKLEQGENVFLQATDKNS
c1qc-121    --NLCVLLYRS----GVKVVTFCG---HTSK-TNQVNSGGVLLRLQVGEEVWLAVNDYYD
mul-1160    --HISGFLVVDG----IDKLAFESENINSEIHCDRVLTGDALLELNYGQEVWLRLAKGTI
cer-64      RQTIQVSLMLNG---WPVISAFAG---DQDV-TREAASNGVLIQMEKGDRAYLKLE-RGN
apm1-115    --DVKVSLFKKD---KAMLFTYDQ---YQEN-NVDQASGSVLLHLEVGDQVWLQVYGEGE
adQ-118     --DVKVSLFKKD---KAVLFTYDQ---YQEK-NVDQASGSVLLHLEVGDQVWLQVYGDGD
acrp-118    --DVKVSLFKKD---KAVLFTYDQ---YQEK-NVDQASGSVLLHLEVGDQVWLQVYGDGD
                                                                     * c1qa-117    HIYQGSE--ADSVFSGFLIFPSA        245
c1qb-122    LLGMEG---ANSIFSGFLLFPDMEA      244
c1qc-121    MVGIQG---SDSVFSGFLLFPD         244
mul-1160    PAKFPP----VTTFSGYLLYRT         1286
cer-64      LMGGWK----YSTFSGFLVFPL         193
apm1-115    RNGLYADNDNDSTFTGFLLYHDTN       244
adQ-118     HNGLYADNVNDSTFTGFLLFHDTN       247
acrp-118    HNGLYADNVNDSTFTGFLLYHDTN       247
                       . *.*.*..
```

FIGURE 3

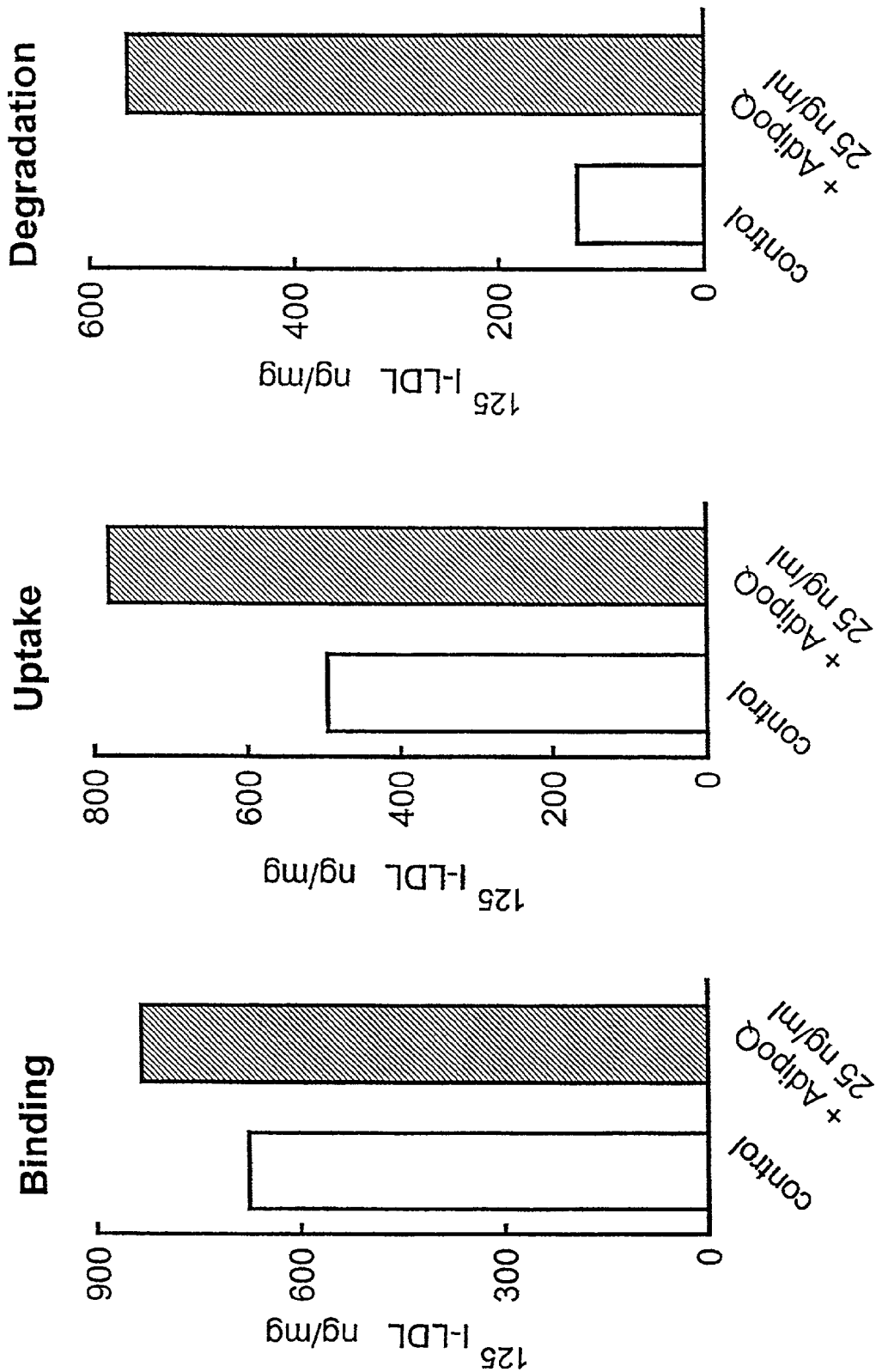

LIPOPROTEIN-REGULATING MEDICANTS

This application is a divisional application of U.S. Ser. No. 09/485,316, filed Feb. 4, 2000, now U.S. Pat. No. 6,344,441, which claimed priority under 35 U.S.C. §371 to PCT/IB98/01256, filed Aug. 6, 1998, which claimed priority on French Patent Application No. 97 10088, filed Aug. 6, 1997, and to Application No. 98 05032, filed Apr. 22, 1998, the entire disclosures of which are incorporated herein by reference.

FIELD OF THE INVENTION

The present invention relates to medicaments that are useful for modulating lipoprotein levels in vivo. More particularly, the invention relates to medicaments that modify the activity of the Lipolysis Stimulated Receptor (LSR) and that can be used to influence the partitioning of dietary lipids between the liver and peripheral tissues, including adipose tissue.

BACKGROUND OF THE INVENTION

Obesity is a public health problem which is both serious and widespread. One third of the population in industrialized countries has an excess weight of at least 20% relative to the ideal weight. The phenomenon continues to worsen, particularly in regions of the globe where economies are modernizing. In the United States, the number of obese people has escalated from 25% at the end of the 70s to 33% at the beginning of the 90s.

Obesity considerably increases the risk of developing cardiovascular or metabolic diseases. It is estimated that if the entire population had an ideal weight, the risk of coronary insufficiency would decrease by 25% and that of cardiac insufficiency and of cerebral vascular accidents by 35%. Coronary insufficiency, atheromatous disease and cardiac insufficiency are at the forefront of the cardiovascular complications induced by obesity. For an excess weight greater than 30%, the incidence of coronary diseases is doubled in subjects under 50 years. Studies carried out for other diseases are equally eloquent. For an excess weight of 20%, the risk of high blood pressure is doubled. For an excess weight of 30%, the risk of developing a non-insulin-dependent diabetes is tripled. That of hyperlipidemias is multiplied six fold.

The list of diseases having onsets promoted by obesity is long: hyperuricemia (11.4% in obese subjects, against 3.4% in the general population), digestive pathologies, abnormalities in hepatic functions, and even certain cancers.

Whether the physiological changes in obesity are characterized by an increase in the number of adipose cells, or by an increase in the quantity of triglycerides stored in each adipose cell, or by both, this excess weight results mainly from an imbalance between the quantities of calories consumed and those of the calories used by the body. Studies on the causes of this imbalance have been in several directions. Some have focused on studying the mechanism of absorption of foods, and therefore the molecules which control food intake and the feeling of satiety. Other studies have characterized the pathways through which the body uses its calories.

The treatments for obesity which have been proposed are of four types. Food restriction is the most frequently used. The obese individuals are advised to change their dietary habits so as to consume fewer calories. This type of treatment is effective in the short-term. However, the recidivation rate is very high. The increase in calorie use through physical exercise is also proposed. This treatment is ineffective when applied alone, but it improves, however, weight-loss in subjects on a low-calorie diet. Gastrointestinal surgery, which reduces the absorption of the calories ingested, is effective but has been virtually abandoned because of the side effects which it causes. The medicinal approach uses either the anorexigenic action of molecules involved at the level of the central nervous system, or the effect of molecules which increase energy use by increasing the production of heat. The prototypes of this type of molecule are the thyroid hormones which uncouple oxidative phosphorylations of the mitochondrial respiratory chain. The side effects and the toxicity of this type of treatment make their use dangerous. An approach which aims to reduce the absorption of dietary lipids by sequestering them in the lumen of the digestive tube is also in place. However, it induces physiological imbalances which are difficult to tolerate: deficiency in the absorption of fat-soluble vitamins, flatulence and steatorrhoea. Whatever the envisaged therapeutic approach, the treatments of obesity are all characterized by an extremely high recidivation rate.

The molecular mechanisms responsible for obesity in man are complex and involve genetic and environmental factors. Because of the low efficiency of the treatments known up until now, it is urgent to define the genetic mechanisms which determine obesity, so as to be able to develop better targeted medicaments.

More than 20 genes have been studied as possible candidates, either because they have been implicated in diseases of which obesity is one of the clinical manifestations, or because they are homologues of genes involved in obesity in animal models. Situated in the 7q31 chromosomal region, the OB gene is one of the most widely studied. Its product, leptin, is involved in the mechanisms of satiety. Leptin is a plasma protein of 16 kDa produced by the adipocytes under the action of various stimuli. Obese mice of the ob/ob type exhibit a deficiency in the leptin gene; this protein is undetectable in the plasma of these animals. The administration of leptin obtained by genetic engineering to ob/ob mice corrects their relative hyperphagia and allows normalization of their weight. This anorexigenic effect of leptin calls into play a receptor of the central nervous system: the ob receptor which belongs to the family of class 1 cytokine receptors. The ob receptor is deficient in obese mice of the db/db strain. The administration of leptin to these mice has no effect on their food intake and does not allow substantial reduction in their weight. The mechanisms by which the ob receptors transmit the signal for satiety are not precisely known. It is possible that neuropeptide Y is involved in this signalling pathway. It is important to specify at this stage that the ob receptors are not the only regulators of appetite. The Melanocortin 4 receptor is also involved since mice made deficient in this receptor are obese (Gura, *Science* 275: 751 (1997)).

The discovery of leptin and the characterization of the leptin receptor at the level of the central nervous system have opened a new route for the search for medicaments against obesity. This model, however, rapidly proved disappointing. Indeed, with only one exception (Montague et al., *Nature* 387:903 (1997)), the genes encoding leptin or its ob receptor have proved to be normal in obese human subjects. Furthermore and paradoxically, the plasma concentrations of leptin, the satiety hormone, are abnormally high in most obese human subjects.

Clearly there remains a need for novel medicaments that are useful for reducing body weight in humans. Such a pharmaceutical composition advantageously would help to control obesity and thereby alleviate many of the cardiovascular consequences associated with this condition.

SUMMARY OF THE INVENTION

One aspect of the present invention relates to an agent which influences the partitioning of dietary lipids between the liver and peripheral tissues for use as a medicament. In one embodiment, this agent can be used for treating a condition in which it is desirable to increase the partitioning of dietary lipids to the liver, reducing food intake in obese individuals, reducing the levels of free fatty acids in obese individuals, decreasing the body weight of obese individuals, or treating an obesity related condition selected from the group consisting of obesity-related atherosclerosis, obesity-related insulin resistance, obesity-related hypertension, microangiopathic lesions resulting from obesity-related Type II diabetes, ocular lesions caused by microangiopathy in obese individuals with Type II diabetes, and renal lesions caused by microangiopathy in obese individuals with Type II diabetes. According to another embodiment of the invention, the agent which influences the partitioning of dietary lipids between the liver and peripheral tissues is any one of: AdipoQ analogues, AdipoQ homologs, AdipoQ derivatives or fragments of any of the preceding agents. In yet another embodiment the agent includes an LSR antagonist or an LSR agonist.

Another aspect of the invention relates to a polypeptide that includes a consensus sequence selected from the group consisting of SEQ ID NO:1 and SEQ ID NO:2 for use as a medicament.

Yet another aspect of the invention relates to a polypeptide comprising an amino acid sequence which alternatively may have at least 25% homology to one of the sequences of SEQ ID NOs.: 7–14, at least 50% homology to one of the sequences of SEQ ID NOs.: 7–14 or at least 80% homology to one of the sequences of SEQ ID NOs: 7–14 for use as a medicament.

Still yet another aspect of the invention relates to a C1q polypeptide, derivative, homologue or a fragment of any of the preceding compounds for use as a medicament.

A further aspect of the invention relates to an AdipoQ polypeptide or a derivative or homologue thereof or a fragment thereof for use as a medicament.

Another aspect of the invention relates to an ApM1 polypeptide or a derivative or homologue thereof or a fragment thereof for use as a medicament.

Still another aspect of the invention relates to the use of a compound that influences the partitioning of dietary lipids between the liver and peripheral tissues in the manufacture of a medicament for treating a condition in which the partitioning of dietary lipids to the liver is abnormal or higher than is desirable. In one embodiment, this medicament can be used for reducing food intake in obese individuals, reducing the levels of free fatty acids in obese individuals, decreasing the body weight of obese individuals, or treating an obesity related condition selected from the group consisting of obesity-related atherosclerosis, obesity-related insulin resistance, obesity-related hypertension, microangiopathic lesions resulting from obesity-related Type II diabetes, ocular lesions caused by microangiopathy in obese individuals with Type II diabetes, and renal lesions caused by microangiopathy in obese individuals with Type II diabetes. According to a different embodiment, the compound is one that is selected is any of: AdipoQ analogues, AdipoQ homologs, AdipoQ derivatives, and fragments of any of the preceding agents. According to yet a different embodiment the compound is an agonist or antagonist of the Lipolysis Stimulated Receptor. According to still another embodiment the compound can be any polypeptide comprising an amino acid sequence having at least 25% homology to one of the sequences of SEQ ID NOs.: 7–14, at least 50% homology to one of the sequences of SEQ ID NOs.: 7–14 or at least 80% homology to one of the sequences of SEQ ID NOs: 7–14 According to a different embodiment, the compound is a polypeptide that specifically binds a γ subunit of the Lipolysis Stimulated Receptor or a gC1q-R or a gC1q-R homologue, but the compound is not a subunit of the Lipolysis Stimulated Receptor. In this instance, the compound includes a polypeptide that can be C1q, AdipoQ, ApM1, Acrp 30, cerebellin or multimerin, or fragments of any of these polypeptides. In another embodiment, the compound that influences the partitioning of dietary lipids between the liver and peripheral tissues can be a polypeptide having binding specificity for a γ subunit of the Lipolysis Stimulated Receptor or a gC1q-R or a gC1q-R homologue for the treatment of obesity. In this instance, the polypeptide is not a subunit of the Lipolysis Stimulated Receptor. According to another embodiment, the polypeptide can have about 25% homology to an ApM1 protein, about 50% homology to an ApM1 protein or about 80% homology to an ApM1 protein. More particularly, the polypeptide can be any of C1q, AdipoQ, ApM1, Acrp 30, cerebellin or multimerin, or fragments of any of these polypeptides. Additionally, the polypeptide can be a human polypeptide, and can be the ApM1 polypeptide or a fragment of the ApM1 polypeptide.

Another aspect of the invention relates to a polypeptide that specifically binds the gC1q-R protein for use in the treatment of obesity, wherein the polypeptide is not a subunit of the Lipolysis Stimulated Receptor. In one embodiment, the polypeptide can be any of C1q, AdipoQ, ApM1, Acrp 30, cerebellin or multimerin.

A still further aspect of the invention relates to a composition for modulating activity of the Lipolysis Stimulated Receptor. This composition includes a compound having binding specificity for the gC1q-R protein, but the compound cannot be a subunit of the Lipolysis Stimulated Receptor. The invented composition also includes a pharmaceutically acceptable carrier.

Another aspect of the invention relates to a composition for modulating activity of the Lipolysis Stimulated Receptor. This composition includes: (1) a polypeptide comprising an amino acid sequence at least 25% homologous to a sequence selected from the group consisting of any one of SEQ ID NOs 7–14, and a pharmaceutically acceptable carrier.

Still another aspect of the invention relates to a composition for modulating the activity of the Lipolysis Stimulated Receptor and includes: (1) a polypeptide that includes a consensus sequence that is either SEQ ID NO:1 or SEQ ID NO:2, and a pharmaceutically acceptable carrier.

Another aspect of the invention relates to a method of reducing plasma lipoprotein levels in an animal. This method includes the steps of: first identifying an animal having a measurable plasma lipoprotein level, then administering to the animal a composition that includes a pharmaceutically acceptable carrier and a polypeptide that is at least 25% homologous to an ApM1 protein and finally allowing passage of a period of time to permit reduction in the measurable plasma lipoprotein level. In a particular case the animal is a mammal. In a particular embodiment the composition may be administered by injection, for example by injecting intravenously. Alternatively, the composition may be administered by surgically implanting an infusion device that slowly releases the composition.

Another aspect of the invention relates to a method of identifying candidate pharmaceutical agents for reducing plasma triglyceride levels in an animal. This method involves first identifying a compound that includes a consensus sequence that may be either SEQ ID NO:1 or SEQ ID NO:2, obtaining a test animal having an initial level of plasma triglycerides, administering the compound to the test animal, waiting for a period of time, measuring a post-treatment level of plasma triglycerides in a blood sample obtained from the test animal and thereafter identifying as candidate pharmaceutical agents any compound that results in a post-treatment level of plasma triglycerides that is lower than the initial level. In one embodiment the test animal is a mammal and the method may involve feeding a high-fat meal to this mammal. The high-fat meal can include about 60% fat, about 20% protein, and about 20% carbohydrate. The fat component may include about 37% saturated fatty acids, about 36% polyunsaturated fatty acids and about 36% polyunsaturated fatty acids.

Still another aspect of the invention relates to a method for treating an animal having a condition in which it is desirable to increase the partitioning of dietary lipids to the liver. This method includes the step of administering an LSR agonist to the animal having the condition.

Still yet another aspect of the invention relates to a method for treating an animal having a condition in which it is desirable to decrease the partitioning of dietary lipids to the liver. This method includes the step of administering an LSR antagonist to the animal having the condition.

In another apsect, the invention comprises an agent which increases the activity of a compound which increases the partitioning of dietary lipids to the liver for use as a pharmaceutical. In one embodiment of this aspect, the agent is for use in reducing food intake in obese individuals, reducing the levels of free fatty acids in obese individuals, decreasing the body weight of obese individuals, or treating an obesity related condition selected from the group consisting of atherosclerosis (whether obesity-related or not), obesity-related insulin resistance, obesity-related hypertension, microangiopathic lesions resulting from obesity-related Type II diabetes, ocular lesions caused by microangiopathy in obese subjects with Type II diabetes, and renal lesions caused by microangiopathy in obese subjects with Type II diabetes. In another embodiment of this aspect, the agent increases the activity of adipoQ, ApM1, a compound analogous to adipoQ or ApM1, or the LSR receptor. In a further embodiment of this aspect, the agent is selected from the group consisting of derivatives of adipoQ, ApM1, C1q, derivatives of a compound analogous to any of the preceding compounds wherein the derivatives exhibit greater activity than the corresponding wild type protein and antibodies capable of specifically binding the γ subunit, the C1q receptor (gC1q-R) or a protein related thereto. In yet another embodiment of this apsect the agent is selected from the group consisting of derivatives of compounds comprising at least one of the sequences of SEQ ID NOs.: 1 and 2, derivatives of compounds comprising an amino acid sequence having at least 25% homology to a sequence selected from the group consisting of SEQ ID NOs. 7–14, derivatives of compounds comprising an amino acid sequence having at least 50% homology to a sequence selected from the group consisting of SEQ ID NOs. 7–14, and derivatives of compounds comprising an amino acid sequence having at least 80% homology to a sequence selected from the group consisting of SEQ ID NOs. 7–14, wherein the derivatives exhibit greater activity than the corresponding wild type protein. In still a further embodiment of this aspect, the agent comprises a nucleic acid encoding a polypeptide or protein which influences the partitioning of dietary lipids between the liver and peripheral tissues for use as a medicament. In another embodiment of this aspect, the nucleic acid encodes a protein or polypeptide selected from the group consisting of adipoQ, ApM1, C1q, polypeptides analogous to ApM, polypeptides having at least one of the consensus sequences of SEQ ID NO: 1 and SEQ ID NO: 2, analogs of any of the preceding polypeptides, homologs of any of the preceding polypeptides, derivatives of any of the preceding polypeptides, and fragments of any of the preceding polypeptides. In still another embodiment of this aspect, the nucleic acid encodes a polypeptide selected from the group consisting of polypeptides comprising an amino acid sequence having at least 25% homology to one of the sequences of SEQ ID NOs.: 7–14, polypeptides comprising an amino acid sequence having at least 50% homology to one of the sequences of SEQ ID NOs.: 7–14, and polypeptides comprising an amino acid sequence having at least 80% homology to one of the sequences of SEQ ID NOs: 7–14. In a further embodiment of this aspect, the agent is selected from the group consisting of small molecules and drugs. In yet another embodiment of this aspect, the agent is for administration to an individual having a below normal level of activity of adipoQ, ApM1, or an analoguous protein.

Another aspect of the present invention is an agent which decreases the activity of a compound which increases the partitioning of dietary lipids to the liver for use as a pharmaceutical. In one embodiment of this aspect, the agent is for use in treating cachexia in subjects with neoplastic or para-neoplastic syndrome or eating disorders. In another embodiment of this aspect, the agent decreases the activity of adipoQ, ApM1, a compound analogous to adipoQ or ApM1, or the LSR receptor. In a further embodiment of this aspect, the agent is an antibody which binds a compound selected from the group consisting of adipoQ, ApM1, C1q, a protein analogous to any of the preceding proteins, a derivative of adipoQ, C1qa, C1qb, C1qc, mul, cer, ApM1, or acrp which inhibits the activity of wild type adipoQ or wild type ApM1, fragments of any of the preceding polypeptides, the γ subunit, the C1q receptor (gC1q-R) or a protein related thereto. In yet another embodiment of this aspect, the agent is an antibody which binds a polypeptide selected from the group consisting of polypeptides comprising at least one of the sequences of SEQ ID NOs.: 1 and 2, polypeptides comprising an amino acid sequence having at least 25% homology to a sequence selected from the group consisting of SEQ ID NOs. 7–14, polypeptides comprising an amino acid sequence having at least 50% homology to a sequence selected from the group consisting of SEQ ID NOs. 7–14, and polypeptides comprising an amino acid sequence having at least 80% homology to a sequence selected from the group consisting of SEQ ID MOs. 7–14. In a further embodiment of this aspect, the agent is selected from the group consisting of antisense nucleic acids to the adipoQ gene, the ApM1 gene or a portion thereof and nucleic acids capable of forming a triple helix with a portion of the adipoQ gene or the ApM1 gene. In yet another embodiment of this aspect, the agent is selected from the group consisting of antisense nucleic acids to a gene encoding a polypeptide comprising at least one of the sequences of SEQ ID NOs.: 1 and 2, a gene encoding a polypeptide comprising an amino acid sequence having at least 25% homology to a sequence selected from the group consisting of SEQ ID NOs. 7–14, a gene encoding a polypeptide comprising an amino acid sequence having at least 50% homology to a sequence selected from the group consisting of SEQ ID NOs. 7–14, and a gene encoding a polypeptide comprising an amino acid sequence having at least 80% homology to a sequence selected from the group consisting of SEQ ID NOs. 7–14. In a further embodiment of this aspect, the agent is selected from the group consisting of small molecules and drugs. In a further embodiment of this aspect, the agent is for administration to an individual having a level of adipoQ or ApM1 activity which is above normal.

Another aspect of the present invention is a method for determining whether an obese individual is at risk of suffering from a condition selected from the group consisting of a condition associated with a lower than desirable level of partioning of dietary lipids to the liver, obesity-related atherosclerosis, obesity-related insulin resistance, obesity-related hypertension, microangiopathic lesions resulting from obesity-related Type II diabetes, ocular lesions caused by microangiopathy in obese subjects with Type II diabetes, and renal lesions caused by microangiopathy in obese subjects with Type II diabetes, comprising the step of determining whether the individual has a lower than normal level of adipoQ activity, ApM1 activity, or activity of a compound analogous thereto.

Another aspect of the present invention is a method for increasing the partitioning of dietary lipids to the liver comprising administering an agent which increases the activity of a compound selected from the group consisting of adipoQ, ApM1, C1q, compounds analogous to C1q, compounds comprising at least one sequence selected from the group consisting of SEQ ID NO:1 and SEQ ID NO:2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14 to an individual. In one embodiment of this aspect, the individual suffers suffers from a condition selected from the group consisting of obesity, obesity-related atherosclerosis, obesity-related insulin resistance, obesity-related hypertension, microangiopathic lesions resulting from obesity-related Type II diabetes, ocular lesions caused by microangiopathy in obese subjects with Type II diabetes, and renal lesions caused by microangiopathy in obese subjects with Type II diabetes. In another embodiment of this aspect, the agent is selected from the group consisting of a derivative of adipoQ, ApM1 or an analogous compound which exhibits greater activity than the corresponding wild type protein, nucleic acids encoding adipoQ, ApM1, or an analogous compound, fragments of any of the preceding compounds, and nucleic acids encoding a derivative of adipoQ, ApM1, or an analogous compound having greater activity than the corresponding wild type protein, and fragments of any of the preceding compounds. In a further aspect of this embodiment, the agent is administered if it is determined that the level of ApM1, or an analogous protein in the individual is below normal.

Another aspect of the present invention is a method for decreasing the partitioning of dietary lipids to the liver comprising administering an agent which decreases the activity of a compound selected from the group consisting of adipoQ, ApM1, C1q, compounds analogous to C1q, compounds comprising at least one sequence selected from the group consisting of SEQ ID NO:1 and SEQ ID NO:2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14 to an individual. In one embodiment of this aspect, the individual suffers from a condition selected from the group consisting of cachexia in subjects with neoplastic or paraneoplastic syndrome or eating disorders. In another embodiment of this aspect, the agent is selected from the group consisting of an antibody which binds adipoQ, ApM1, C1q or an analogous protein, a derivative of adipoQ, C1qa, C1qb, C1qc, mul, cer, ApM1, or acrp which inhibits the activity of wild type adipoQ or wild type ApM1, a fragment of the derivative, antisense nucleic acids to the adipoQ gene, the ApM1 gene or a portion thereof, nucleic acids capable of forming a triple helix with a portion of the adipoQ gene or the ApM1 gene, and antibodies capable of binding the γ subunit, the C1q receptor (gC1q-R) or a protein related thereto. In still another embodiment of this aspect, the agent is administered if it is determined that the level of adipoq, ApM1, or an analogous protein in the individual is above normal.

Another aspect of the present invention is a method of identifying a candidate compound for regulating the partitioning of dietary lipids between the liver and the adipose tissue comprising the steps of contacting the γ subunit, the C1q receptor (gC1q-R) a protein related thereto, or a fragment thereof with one or more molecules to be tested for binding activity under conditions which permit specific binding of the molecule to the γ subunit, C1q receptor (gC1q-R), protein related thereto, or fragment thereof and determining whether the one or more molecules bind to the γ subunit, C1q receptor (gC1q-R), protein related thereto, or fragment thereof. In one embodiment of this aspect, the contacting step is performed using a cell expressing the γ subunit, C1q receptor (gC1q-R), protein related thereto, or fragment thereof. In another embodiment of this aspect, the γ subunit, C1q receptor (gC1q-R), protein related thereto, or fragment thereof is immobilized on a support. In yet another embodiment of this aspect, the method further comprises contacting the γ subunit, C1q receptor (gC1q-R), protein related thereto, or fragment thereof with a known ligand and determining the ability of the one or more molecules to be tested for binding activity to compete with the known ligand for binding to the γ subunit, C1q receptor (gC1q-R), protein related thereto, or fragment thereof. In a further embodiment of this aspect, the molecule to be tested for binding to the γ subunit, C1q receptor (gC1q-R), protein related thereto, or fragment thereof is selected from the group consisting of polypeptides, peptides, derivatives or analogs thereof, drugs, and small molecules.

Another aspect of the invention relates to a method of identifying candidate pharmaceutical agents for reducing plasma triglyceride levels in an animal. This method involves first administering a compound to a test, and measuring a post-treatment level of plasma triglycerides in a blood sample obtained from the test animal. In one embodiment the test animal is a mammal and the method may involve feeding a high-fat meal to this mammal. The high-fat meal can include about 60% fat, about 20% protein, and about 20% carbohydrate. The fat component may include about 37% saturated fatty acids, about 36% polyunsaturated fatty acids and about 36% polyunsaturated fatty acids.

BRIEF DESCRIPTION OF THE DRAWING

FIG. 3 shows an alignment of several proteins that are analogous to C1q. The globular domains of proteins belonging to the C1q complement family were aligned using clustalW. The various aligned sequences are:

Figure 1:
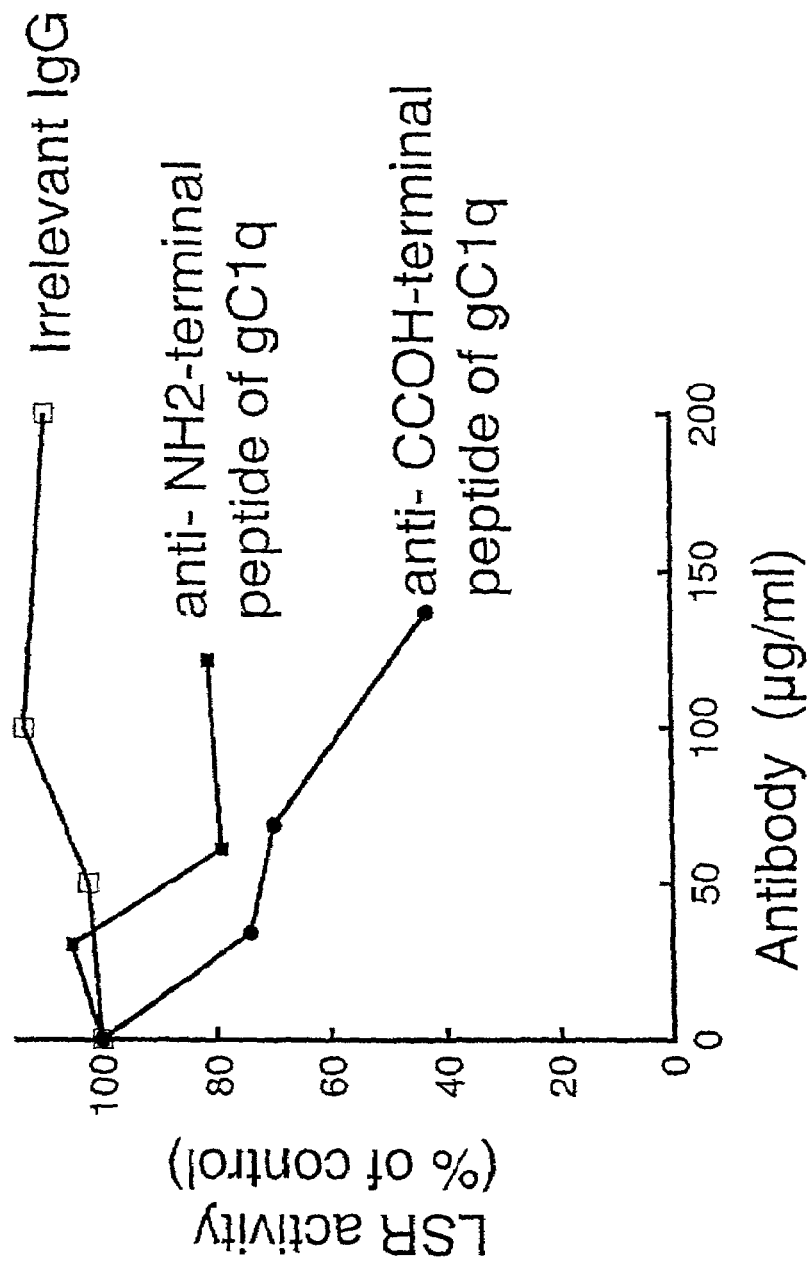
FIG. 1 is a line graph showing the inhibitory effect of antibodies directed against synthetic peptides representing the amino-terminal and carboxy-terminal regions of the gC1q-R protein. Oleate-induced binding of $^{125}$I-LDL to rat hepatocyte plasma membranes was measured in the presence of increasing concentrations of antibodies directed against an amino-terminal peptide of gC1q-R (■); antibodies directed against a carboxy-terminal peptide of gC1q-R (○) or a negative control antibody (□).

C1qa-117: protein sequence of complement C1q A (reference Swiss Prot: P02745), from the amino acid at position 117 (SEQ ID NO:7)

C1qb-122: protein sequence of complement C1q B (reference Swiss Prot: P02746), from the amino acid at position 122 (SEQ ID NO:8)

C1qc-121: protein sequence of complement C1q C (reference Swiss Prot: P02747), from the amino acid at position 121 (SEQ ID NO:9)

mul-1160: protein sequence translated from the nucleic sequence for multimerin (GenBank, Accession: U27109) from amino acid 1160 (SEQ ID NO:14)

cer-64: protein sequence translated from the nucleic sequence for cerebellin (GenBank, Accession: M58583) from amino acid 64 (SEQ ID NO:10)

apm1-115: protein sequence translated from the nucleic sequence for ApM1 (GenBank, Accession: D45371) from amino acid 115 (SEQ ID NO:11)

adQ-118: protein sequence translated from the nucleic sequence for AdipoQ (Genbank, Accession: U49915) from amino acid 118 (SEQ ID NO:12)

acrp-118: protein sequence translated from nucleic sequence for acrp30 (GenBank, Accession: U37222) from amino acid 118 (SEQ ID NO:13).

Boxed sequences show the two portions of alignment corresponding to the C1q signature, the first corresponding to the consensus deposited in the Prosite data base (#PDOC00857): F-x(5)-[N/D]-x(4)·[F/Y/W/L]-x(6)-F-x(5)-G-x-Y-x-F-x-[F/Y] (SEQ ID NO:1), the second at the COOH-end of the proteins is: [S/T]-x-F-[S/T]-G-[F/Y]-L-[L/V]·[F/Y] (SEQ ID NO:2). In these sequences, the square brackets ([]) enclose alternative amino acids that ran occupy a position and numbers indicate the number of iterations of an unspecified amino acid. The arrows (V) above the alignments mark the positions of the cystein residues conserved in the three forms of C1q but not in the other aligned proteins. The symbols (*) placed under the alignments indicate the conserved amino acids, the symbols (.) indicate the conservative substitutions of amino acids.

FIGS. 4A–4C show bar graphs representing different aspects of LSR activity. The graphs show results for (A) binding; (B) uptake or internalization; and (C) degradation of $^{125}$I-LDL by cultured hepatocytes. Open bars represent the difference between values obtained after incubation with and without 0.6 mM oleate in the absence of AdipoQ. Closed bars show the same parameters in samples incubated with 25 ng AdipoQ.

Figure 5:
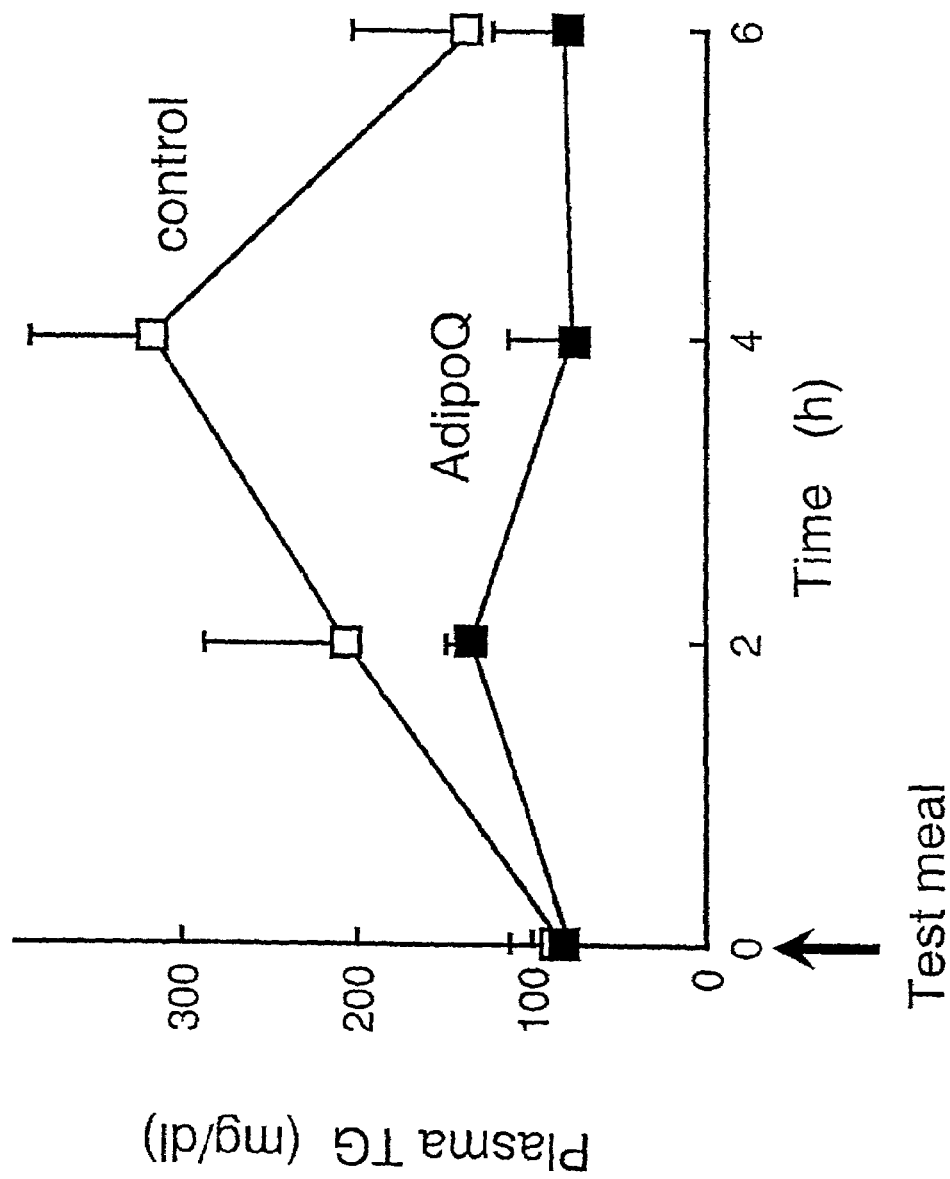

FIG. 5 is a line graph showing the postprandial lipemic response in rats injected with AdipoQ.

Figure 6B:
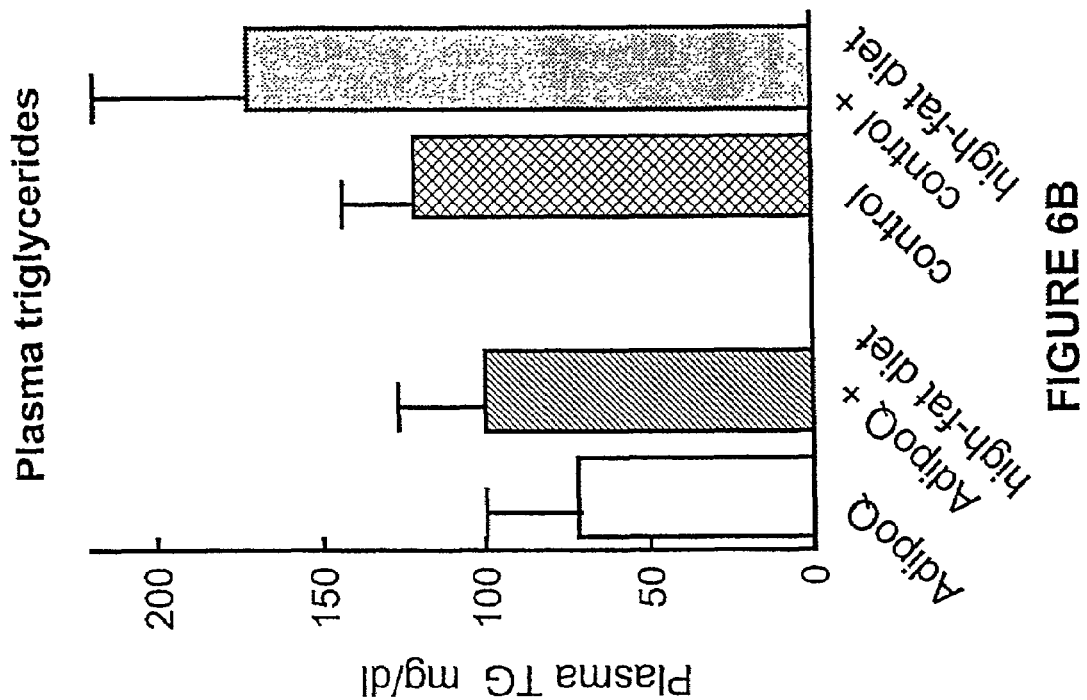
Figure 6A:
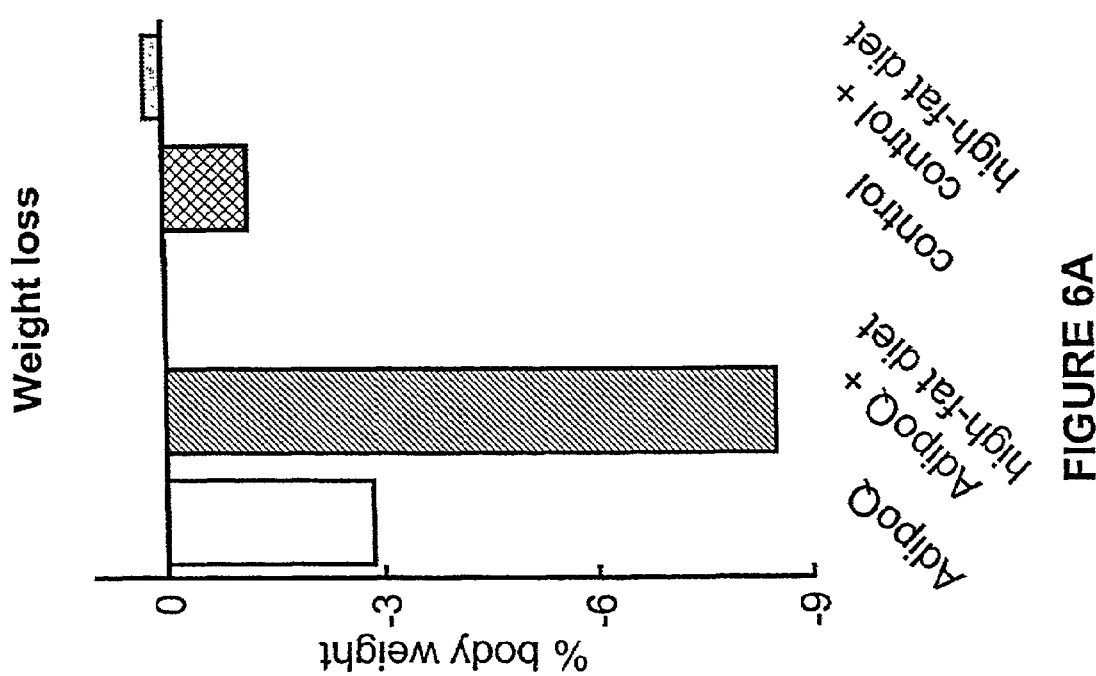

FIGS. 6A–6B are bar graphs representing results obtained following infusion of AdipoQ in rats. The graphs show results for (A) weight loss; and (B) plasma triglyceride levels.

Figure 7B:
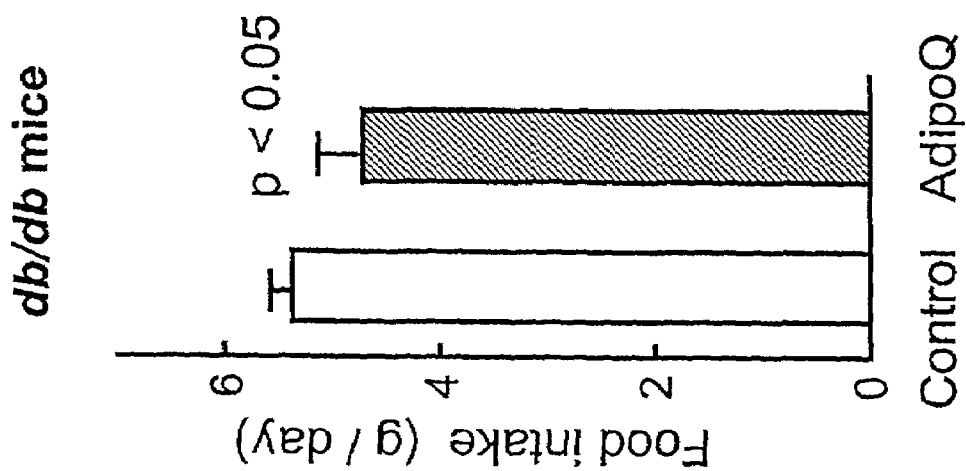
Figure 7A:
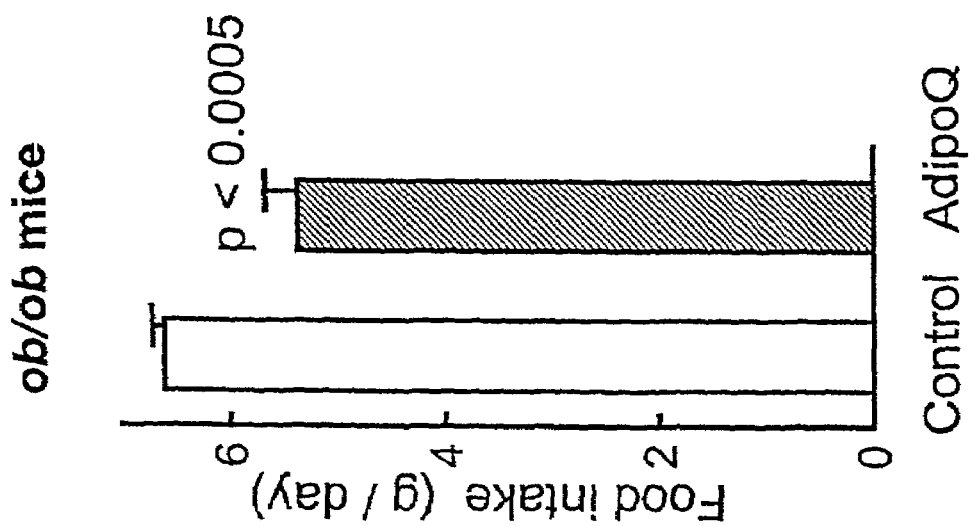

FIGS. 7A–7B are bar graphs representing daily food intake for (A) ob/ob mice; and (B) db/db mice that were either controls or administered with AdipoQ.

DETAILED DESCRIPTION OF THE PREFERRED EMBODIMENT

Overview

Herein we disclose compositions and methods that are useful for modulating the activity of the "Lipolysis Stimulated Receptor" (LSR). As detailed below, the ability to modulate LSR activity provides a means for intervening in pathologies that involve abnormalities in lipid metabolism. More particularly, we have discovered a family of compounds that can be incorporated into medicaments which, when administered in vitro or in vivo, advantageously enhance LSR activity. As a consequence, lipoproteins are efficiently bound, internalized and degraded by hepatocytes.

When used in this fashion, compounds that enhance LSR activity, particularly those that enhance receptor activity can promote weight loss. In contrast to LSR-activating compounds, agents that inhibit LSR activity can be used to promote lipid storage in adipose tissue because lipoprotein degradation by the liver will be reduced. The invented compositions and methods are useful for treating conditions that include: obesity and anorexia, hyperlipidemias, atherosclerosis, diabetes, hypertension, and more generally the various pathologies associated with abnormalities in the metabolism of cytokines.

Introduction

The present invention relates generally to methods and compositions that are useful for regulating the activity of a multi-subunit receptor called LSR. The LSR is expressed on the surface of hepatic cells and binds lipoproteins in the presence of free fatty acids. In the absence of free fatty acids the LSR can bind a cytokine, preferably leptin. Importantly, the LSR is also capable of binding gC1q-R (Ghebrehiwet et al., *J. Exp. Med.* 179:1809 (1994)) or a gC1q-R-like receptor. Those having ordinary skill in the art will understand that the gC1q-R is a receptor for C1q, a protein that is a key component of the complement system and that is also known to activate phagocytosis by macrophages.

In brief, the LSR includes at least one α and one β subunit, preferably one α and three β subunits. Both α and β subunits are the translation products of two mRNA species that result from alternative splicing of a common precursor RNA. An α' (alpha prime) subunit, which is an integral membrane protein like the α subunit and is encoded by a third alternatively spliced mRNA, is believed to be a constituent of LSR in the alternative to the α subunit. Further inclusion of a γ subunit, which may be gC1q-R or a gC1q-R-like receptor protein, with the LSR results in the formation of "LSR complex." We postulate that the gC1q-R or the gC1q-R-like protein serves as a molecular chaperon that associates with LSR.

We believe that agents which modify the structure of the LSR complex by perturbing interaction of the γ subunit with the LSR effectively activate the LSR in the absence of free fatty acids. The effect of this perturbation can be measured as increased hepatocyte binding, internalization and degradation of lipoproteins. When lipids are degraded within liver cells, fewer lipids are available for uptake and storage by adipose tissue.

Definitions

As used herein, the terms "LSR" and "LSR receptor" refer to the combination of α or α' and β subunits that make up a receptor primarily expressed on the surface of hepatocytes and that can bind and facilitate the internalization and degradation of lipoproteins by hepatocytes.

As used herein, "LSR complex" refers to an LSR receptor which further includes a γ subunit.

As used herein, the term polypeptide is understood to designate a protein or a peptide.

Equivalent polypeptide will be understood to mean a polypeptide having at least one of the activities of a subject polypeptide. Thus, for example, if a subject polypeptide is able to inhibit binding of a γ subunit to the LSR to form an LSR complex, then in this context an equivalent polypeptide will be a polypeptide that similarly is able to inhibit binding of the γ subunit to the LSR.

Homologous polypeptide will be understood to mean polypeptides that exhibit certain modifications when compared with the natural polypeptide. These modifications include a deletion, truncation, extension, chimeric fusion and/or mutation, in particular a point mutation. Among the homologous polypeptides, those in which the amino acid sequence exhibits at least 80%, preferably 90%, homology with the amino acid sequences of the polypeptides according to the invention are preferred.

Derivative polypeptide (or derivative protein) will be understood to mean all the mutated polypeptides which may exist, including truncations, deletions and/or additions of amino acid residues (including naturally occurring amino acids, modified and unusual amino acids such as those listed in Table 4 of WIPO Standard ST.25 (1998), and non-naturally occurring amino acids), substitutions or mutations, in particular point mutations, regardless of whether they are naturally occurring or whether they have been artificially. Artificially generated derivates may be created using a variety of techniques, including mutagenesis of nucleic acids encoding the polypeptides, chemical synthesis, or chemical modification.

As used herein the terms "obesity" and "obesity-related" are used to refer to individuals having a body mass which is measurably greater than ideal for their height and frame. Preferably, these terms refer to individuals with body mass index values of greater than 10, more preferably with body mass index values of greater than 20, and most preferably with body mass index values of greater than 35.

Polypeptide fragment is understood to mean a polypeptide or a peptide comprising at least 5, at least 7, at least 10, at least 15, at least 30, or more than 30 consecutive amino acids of the polypeptide from which they are derived. It will be understood that a polypeptide fragment may be obtained from a derivative polypeptide.

Biologically active fragments of a polypeptide will be understood to mean a portion of a larger polypeptide wherein said portion retains an activity characteristic of the larger polypeptide, and wherein the activity is measurable in any biological system. For example, a polypeptide fragment is deemed to be "biologically active" if it demonstrates a statistically significant change in activity in any of the assays described in Examples 1, 2, 6, 7, 8, 9 or 10. Thus, for example, if a protein characteristically modifies the interaction between the γ subunit and the LSR receptor, then a biologically active fragment of that protein would be a portion of the protein that retains the ability to modify said interaction.

A polynucleotide, nucleic sequence or nucleic acid is understood to mean an isolated natural or synthetic DNA and/or RNA molecule which may include non-natural nucleotides.

Equivalent polynucleotide sequences are understood to mean nucleic acid sequences encoding the polypeptides according to the invention, taking into account the degeneracy of the genetic code, the complementary DNA sequences and the corresponding RNA sequences, as well as the nucleic acid sequences encoding the equivalent polypeptides.

Homologous nucleic sequences are understood to mean the nucleic sequences encoding the homologous polypeptides and/or the nucleic sequences exhibiting a level of homology of at least 80%, preferably 90%. According to the invention, the homology is only of the statistical type, it means that the sequences have a minimum of 80%, preferably 90%, of nucleotides in common.

Allele or allelic variant will be understood to mean the natural mutated sequences corresponding to polymorphisms present in human beings and, in particular, to polymorphisms which can lead to the onset and/or to the development of obesity or of anorexia. These polymorphisms can also lead to the onset and/or to the development of risks or complications associated with obesity, in particular at the cardiovascular level, and/or of pathologies associated with abnormalities in the metabolism of cytokines.

Mutated nucleic sequences are understood to mean the nucleic sequences comprising at least one point mutation compared with the normal sequence.

While the sequences according to the invention are in general wild type sequences, they are also mutated sequences since they comprise at least one point mutation and preferably at most 10% of mutations compared with the wild type sequence.

As referred to herein, methods and medicaments of the invention can be used for treating animals, including birds, fish and mammals. It is to be understood that the category of mammals includes mammals such as mice, rats, rabbits, domesticated mammals and human beings. Although the methods of treatment can be applied to non-human mammals, we clearly envision that humans can also be treated using the methods and medicaments disclosed herein.

LSR Activity-Modulating Compounds

Using the methods disclosed herein, compounds that selectively modulate the activity of the LSR in vitro and in vivo have been identified. The compounds identified by the process of the invention include, for example, antibodies having binding specificity for the gC1q-R protein, C1q and AdipoQ. Since ApM1 is reasonably expected to represent the human homologue of murine AdipoQ, as described below, it follows that ApM1 will be useful for modulating LSR activity and lipoprotein metabolism in humans. More generally, it is expected that homologues of C1q will be useful for modulating LSR activity and lipoprotein metabolism. The compounds of the present invention, however, are not limited to any particular chemical structure, as they are solely defined by the assay cascade of the invention, which allows, for the first time, for systematic and rational identification of highly potent and selective modulators of the hepatocyte-specific LSR on a molecular level.

Indications

While not wishing to be bound by any particular theory of operation, the compounds identified by the methods of the present invention are believed to bind to the γ subunit of the LSR complex whereat the compound either will enhance or inhibit LSR activity. Thus, pharmaceutical compositions comprising a therapeutically effective amount of a compound identified by the process of the invention will be useful for the treatment of diseases characterized by high levels of circulating triglycerides or an undesirably strong tendency for lipid deposition at adipose tissue. Alternatively, compounds that inhibit LSR activity will be useful for favoring lipid deposition to the adipose tissue and/or diminishing liver degradation of dietary lipids.

Thus, in general, the disorders which may be treated with the compounds, compositions, medicaments and pharmaceutical formulations identified by the process of the invention generally refer to disorders involving lipid metabolism.

Pharmaceutical Formulations and Routes of Administration

The identified compounds can be administered to a mammal, including a human patient, alone or in pharmaceutical compositions where they are mixed with suitable carriers or excipient(s) at therapeutically effective doses to treat or ameliorate a variety of disorders associated with lipid metabolism. A therapeutically effective dose further refers to that amount of the compound sufficient to result in amelioration of symptoms as determined by the methods described herein. Thus, a therapeutically effective dosage of AdipoQ or ApM1 will be that dosage of the compound that is adequate to promote reduced triglyceride levels following a high-fat meal and that will promote weight loss with continued periodic use or administration. Techniques for formulation and administration of the compounds of the instant application may be found in "Remington's Pharmaceutical Sciences," Mack Publishing Co., Easton, Pa., latest edition.

Routes of Administration

Suitable routes of administration include oral, rectal, transmucosal, or intestinal administration, parenteral delivery, including intramuscular, subcutaneous, intramedullary injections, as well as intratheal, direct intraventricular, intravenous, intraperitoneal, intranasal or intraocular injections. A particularly useful method of administering compounds for promoting weight loss involves surgical implantation, for example into the abdominal cavity of the recipient, of a device for delivering the compound over an extended period of time. Sustained release formulations of the invented medicaments particularly are contemplated.

Composition/Formulation

Pharmaceutical compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically acceptable carrier and at least one polypeptide that is homologous to the C1q protein or a fragment thereof. In addition to medicaments that include protein components homologous to the C1q protein homologues, we also contemplate that non-protein compounds that interact with the γ subunit of the LSR complex also will find utility as modulators of LSR activity, both in vitro and in vivo. Included among examples of C1q protein homologues that will find utility in modulating LSR activity and/or stimulating a reduction of plasma lipoproteins and/or promoting weight loss are: the C1q proteins (C1q A, C1q B and C1q C), AdipoQ, ApM1, acrp 30, cerebellin and multimerin.

For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical formulations for parenteral administration include aqueous solutions of the active compounds in water-soluble form. Aqueous suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to effect enhanced or inhibited LSR activity in an in vitro system. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred.

The data obtained from these cell culture assays and animal studies can be used in formulating a range of dosage for use in human. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to maintain the LSR modulating effects. Dosages necessary to achieve the LSR modulating effect will depend on individual characteristics and route of administration.

Dosage intervals can also be determined using the value for the minimum effective concentration. Compounds should be administered using a regimen which maintains plasma levels above the minimum effective concentration for 10–90% of the time, preferably between 30–90%; and most preferably between 50–90%. In cases of local administration or selective uptake, the effective local concentration of the drug may not be related to plasma concentration.

The amount of composition administered will, of course, be dependent an the subject being treated, on the subject's weight, the severity of the affliction, the manner of administration and the judgment of the prescribing physician.

A preferred dosage range for the amount of polypeptide homolog of C1q, such as AdipoQ or ApM1, that can be administered on a daily or regular basis to achieve desired results, including a reduction in levels of circulating plasma triglycerides and/or lipoproteins, range from 0.1–50 mg/kg body mass. A more preferred dosage range is from 0.2–25 mg/kg. A still more preferred dosage range is from 1.0–20 mg/kg, while the most preferred range is from 2.0–10 mg/kg. Of course, these daily dosages can be delivered or administered in small amounts periodically during the course of a day.

Protein Homologies

It is to be understood that a polypeptide having a given level of homology to a subject protein or polypeptide can be identified using readily available sequence alignment and comparison programs, such as blastp, fasta and/or ClustalW, and methods that will be familiar to those having ordinary skill in the art. One approach for identifying a protein that is homologous to a subject protein involves running a standard "blastp" (Altschul et al., *J. Mol. Biol.* 215:403–410 (1990) sequence comparison algorithm. In this approach, a relatively low score in the blastp algorithm can be used to isolate large numbers of potentially homologous sequences of different lengths. For example, a low score may be on the order of from between about 80 to about 100 and may result in targets having homology levels of about 20%.

If higher levels of homology are desired, additional steps can be taken. For example, once a first series of candidate homologous sequences has been identified, sequences that are more homologous to the subject protein can then be selected. At that stage, two parameters can be varied. First, it is possible to "cut" the subject protein into sub-sequences of interest and then run homology searches that refine the results obtained in the initial step. For example, the fragments that are listed as SEQ ID 7–14 or the consensus sequences within the two boxed regions shown in FIG. 3 could be selected as sub-sequences of interest that could be used to run homology searches. Second, the score used in running the blastp algorithm can be increased. For example, by increasing the score up to a level of about 300, homology levels of about 80% frequently can be obtained. These procedures can be carried out using easily accessible computer programs such as, for example, "blastp" or "fasta". (Altschul at al., *J. Mol. Biol.* 215:403–410 (1990); Pearson, W. R. *G Genomics* 11:635–650 (1991)).

Those having ordinary skill in the art will appreciate that the above-referenced score that can be input into the sequence comparison program can be calculated based on the degree of homology that is being sought. Formulas within the cited packages of computer algorithms allow for this possibility. In general, an increasing score allows for the identification of increasingly specific protein alignments characterized by high levels of homology. Candidate alignments can be further refined using pairwise (fasta) or multiple alignments (ClustalW) (Higgins et al., *Computer Applications in the Biosciences* (*CABIOS*), 8:189–191 (1992) and Thompson et al., Nucleic Acids Research 22: 4673–4680 (1994)).

An illustration of the extent of protein homology appears in Table 1. The results appearing in the table show various homology levels between the ApM1 and various whole proteins or fragments of those proteins. Thus, for example, the entire Acrp 30 protein sequence exhibited 81.8% homology with the ApM1 protein, while the Acrp segment identified by SEQ ID NO:13 showed 91.5% homology with the ApM1 protein.

TABLE 1

Homologies Between ApM1 and Various Proteins

| Protein/<br>SEQ ID NO: | Whole protein | Seq ID Nos: 7–14 |
|---|---|---|
| Acrp 30/<br>SEQ ID NO: 13 | 81.8% | 91.5% |
| AdipoQ/<br>SEQ ID NO: 12 | 80.6% | 90% |
| C1qa/<br>SEQ ID NO: 7 | 32.9% | 27.1% |
| C1qb/<br>SEQ ID NO: 8 | 31.8% | 36.7% |
| C1qc/<br>SEQ ID NO: 9 | 38.8% | 38% |
| Multimerin/<br>SEQ ID NO: 14 | 27.7% | 28.8% |
| Cerebellin/<br>SEQ ID NO: 10 | 24.6% | 28.3% |

In order to identify a protein having a given level of homology, such as at least 25% homology, at least 50% homology, or at least 80% homology to another protein, such as AdipoQ, ApM1 or C1q, one can use a standard blastp analysis in which the program is instructed to recover proteins having a score corresponding to the desired level of homology. For example, to identify proteins having a homology level of 20–30% the program may be instructed to recover proteins having a score from between about 80 to about 100. To recover a protein having an 80% homology level, one can instruct the program to include proteins having a score of about 300. It will be appreciated that these scores may be computed over the full length of the subject protein or over a portion of the protein such as SEQ ID NOs 7–14. It will further be appreciated that homology levels other than those explicitly enumerated herein can be obtained using the instructions provided as part of the program. Thus, the foregoing description is adequate to allow one of ordinary skill in the art to identify polypeptides that are homologous to a subject protein, such as the human ApM1 protein, at various levels of homology. In some cases, the default parameters may be used.

The Multi-subunit LSR

The hepatocyte-specific LSR is a multi-subunit receptor having a dual activity. When activated by free fatty acids, the LSR allows endocytosis of lipoproteins and so is a component in a metabolic pathway for the clearance of lipoproteins. This pathway serves mainly, but not exclusively, to promote clearance of particles high in triglycerides of intestinal origin (Mann et al., *Biochemistry* 34:10421 (1995)). This activity, expressed most particularly at the hepatic level, is dependent on the presence of free fatty acids which bind to the receptor, induce a reversible change in the conformation of this complex and allow it to bind, with a high affinity, various classes of lipoproteins such as those containing apoprotein B or apoprotein E. In its other role, and in the absence of free fatty acids, the LSR does not bind lipoproteins, but is capable of binding a cytokine, in particular leptin. The receptor-bound leptin is then internalized by the hepatocyte where it is degraded.

As described above, the LSR subunits can bind gC1q-R, the receptor for C1q, one of the components of the complex C1 of the conventional pathway for complement activation. Proteins analogous to gC1q-R also can bind at the LSR site for binding of gC1q-R. Proteins analogous to gC1q-R are understood to mean in particular the homologous proteins preferably exhibiting a level of amino acid sequence homology of at least 80%, the proteins exhibiting at least one of the motifs of a site for binding of the protein gC1q-R on the LSR receptor and/or the proteins capable of interacting with the LSR receptor.

Another feature of the LSR relates to the fate of bound lipoproteins or cytokines. More particularly, it is a characteristic of the LSR that bound lipoproteins or bound cytokines are incorporated into the cell and then degraded. The bound lipoproteins may particularly contain apoprotein B or E.

As described in supplemental detail below, activity of the LSR complex can be modulated by a family of compounds that includes C1q or one of its analogous compounds, such as AdipoQ (Hu at al., *J. Biol. Chem.* 271:10697 (1996)), ApM1 (Maeda et al., *Biochem. Biophys. Res. Commun.* 221:286 (1996)) and cerebellin. In particular, the compound C1q or one of its analogous compounds makes it possible, in the absence of free fatty acid, to enhance LSR activity and so to increase the quantity of lipoproteins bound, internalized and degraded by the cells that expresses the LSR receptor.

The invention relates in part to polypeptides or other compounds that are able to modulate, either by mimicking, promoting, inhibiting or otherwise altering the interaction of the $\gamma$ subunit of the LSR complex with the $\alpha$ or $\alpha'$ and $\beta$ subunits of the LSR receptor.

The polypeptides of the invention are obtained by purification or isolation from natural sources or alternatively obtained by genetic recombination, or chemical synthesis. In the case where the polypeptides are synthetic polypeptides, they can contain non-natural amino acids.

A more complete definition of the invention can be made by first describing the structure of the LSR and the methods that were used to elucidate its pharmacological properties.

Defining the Structure and Function of the LSR

The LSR subunits were identified by procedures that employed receptor-specific polyclonal antibodies. These antibodies were obtained by immunizing rabbits with a gel-purified 240 kDa species that bound a labeled LDL probe in a ligand blotting assay (Mann et al., *Biochemistry* 34:10421 (1995)) conducted in the presence of 0.8 mM oleate. In the procedures described herein, oleate is employed as a model free fatty acid used for activating the lipoprotein binding activity of the LSR. Results of this ligand blotting assay further indicated that membrane proteins having estimated molecular weights of 115 kDa and 90 kDa also bound LDL. Notably, the rabbit antibodies recognized all three of the LDL-binding species in a Western blotting procedure, and inhibited the binding of LDLs to LSRs disposed on rat hepatocytes in a ligand binding assay. This indicated that the polyclonal antibodies raised against the 240 kDa LDL-binding species were useful as LSR-specific reagents.

Electrophoretic analysis of proteins that were immunoprecipitated using the anti-LSR antibodies and then separated under reducing conditions indicated that only a very small number of individual proteins were recognized by the antibody reagent. More particularly, it was found that proteins of 68 kDa, 56 kDa and 35 kDa were present in the immunoprecipitate. This demonstrated that the LSR complex was a multimer composed of subunits having molecular weights of 68 kDa (α subunit), 56 kDa (β subunit) and 35 kDa (γ subunit). These molecular weights are estimates and were obtained from the rat. As detailed below, the γ subunit is believed to correspond to a previously known protein. The structures of the α and β subunits were established by an expression cloning procedure using the polyclonal anti-LSR antibodies as a probe.

Indeed, a λgt11 rat liver cDNA library was screened with the LSR-specific antibodies to identify clones expressing proteins corresponding to the LSR subunits. Detailed analysis of one of the isolated phage clones using a PCR protocol based on the identified cloned sequence led to the identification of three different mRNA species. Careful examination of the sequences of these mRNAs, together with subsequent PCR and cloning procedures, confirmed the three species represented alternative splicing variants of a single precursor transcript. The three complete cDNAs had lengths of 2097 bp, 2040 bp and 1893 bp. The molecular weights of the predicted proteins encoded by the open reading frames in the three cDNA sequences were 66 kDa, 64 kDa and 58 kDa, respectively.

Northern blotting procedures using RNA isolated from different rat tissues indicated that the cloned polynucleotide hybridized to transcripts expressed in rat liver as 1.9 kb and 2.1 kb mRNAs, and further indicated that this expression was substantially restricted to liver.

Five different techniques were used to demonstrate that the 2097 bp and the 1893 bp were essential components of the LSR receptor. First, polyclonal antibodies were raised against two synthetic peptides having sequences corresponding to residues 169–186 and to residues 556–570 respectively, encoded by the 2097 bp cDNA. These peptide sequences were common to all of the predicted proteins encoded by the three mRNA splice variants described above. It was shown that these anti-peptide antibodies, but not irrelevant control antibodies, inhibited the binding of LDLs to the LSR present on rat plasma membranes. Second, Western blotting and ligand blotting procedures showed that partially purified α and β subunits: (1) bound the rabbit polyclonal anti-LSR antibodies; (2) bound the anti-peptide antibodies; and (3) bound LDLs after incubation with oleates. Third, in vitro translation and labeling to produce synthetic proteins corresponding to the polypeptides encoded by the 2097 bp and the 1893 bp cDNAs led to products that bound LDL in an ultracentrifugation assay in which LDL binding produced a complex having a density that was lower than the density of the protein alone. This binding was enhanced in the presence of oleate by two fold for the α subunit, or by five fold for the β subunit. Fourth, Chinese hamster ovary cells (CHO) transiently transfected with a plasmid containing the LSR α subunit were found to display an increased binding of LDL after incubations in the presence of oleate while LDL binding measured in the absence of oleate remained unchanged. Cotransfection of plasmids containing the β LSR subunit together with the α LSR subunit further increased the binding of LDL observed after incubations with oleate. Most importantly, an increase in LDL degradation was observed after incubation with oleate only in dishes containing cells cotransfected with the LSR α and β subunits. Therefore, cotransfection of both LSR α and β subunits is a condition sufficient to increase LSR activity in CHO cells. The affinity of the various classes of lipoproteins for the LSR in cells cotransfected with the α and β subunit was very similar to that originally described for the LSR expressed in rat hepatocytes or in human fibroblasts isolated from subjects with familial hypercholesterolemia (Bihain et al., *Biochemistry* 31:4628 (1992); Yen et al., *Biochemistry* 33:1172 (1994)).

A fifth line of evidence demonstrating that the identified gene was responsible for LSR function and that this receptor participates in the clearance of dietary triglycerides was obtained using genetically obese mice. Both ob/ob mice (having a deficient leptin gene) and db/db mice (having a defect in the gene encoding the leptin receptor) were found to exhibit an increased postprandial lipemic response after forced feeding of the standard test meal described above. The apparent number of LSR available on the plasma membrane of hepatocytes of these obese mice was lower than that of the lean controls. Further, analysis by Northern blotting revealed that the level of LSR mRNA was reduced significantly in obese mice. Treatment of the obesity of ob/ob mice by daily administration of recombinant leptin over a thirty day period led to more than a 30% reduction of the animal body weight; to a massive decrease in the postprandial lipemic response; to a significant increase in the apparent number of LSR expressed at the surface of liver cells and to an increased number of LSR mRNA.

On the basis of these data it was therefore established that the identified LSR gene was responsible for the function of this receptor; that the LSR represents a rate limiting step for the clearance of dietary triglycerides and that the expression of this gene is disregulated in obese mice. Moreover, the LSR 56 and 68 kDa subunits substantially bound LDLs only after incubation with oleate. Stoichiometric analysis of immunoprecipitation products indicated that the 240 kDa LDL-binding complex that was observed in the ligand blotting assay most likely represented a multimeric complex formed by a single α and three β subunits. It is believed that the above-described 2040 bp cDNA which represents the third alternative RNA splicing product encodes a subunit that can substitute for α in the multimeric complex. This latter protein is referred to as α' (alpha prime).

While the α and β subunits of LSR were encoded by alternatively spliced mRNAs generated from a single precursor molecule, the expression cloning procedure described above did not provide insight into the identity of the 35 kDa subunit that was detected along with the 68 kDa and 56 kDa proteins in the anti-LSR immunoprecipitate. Indeed, the γ subunit of the LSR was identified by direct sequencing of the purified protein.

More particularly, N-terminal sequencing of immunoaffinity purified material was used to establish the likely identity of the final component of the LSR complex. In this procedure column-immobilized polyclonal rabbit anti-LSR antibodies were used to capture membrane proteins from rat liver. After verifying the presence of the 35 kDa species in the column eluate, a sample containing the 35 kDa protein was sequenced using a standard Edman degradation protocol. Results from this procedure gave a 19 amino acid long polypeptide sequence that was used to search a protein data base. This search revealed that the γ subunit of the LSR receptor included a polypeptide sequence that identically appeared in gC1q-R (Ghebrehiwet et al., *J. Exp. Med.* 179:1809 (1994)), a known cell surface receptor that binds the globular heads of C1q. Since the entire sequence of the immunoaffinity purified 35 kDa protein was not established, we allow the possibility that the γ subunit of the LSR complex is related, but not identical to the gC1q-R protein.

Analysis of the protein sequences of the α and β subunits of the LSR revealed several interesting structural features. For example, the presence of several phosphorylation sites at the N-terminal end of the α subunit protein suggested that the amino terminus of this protein was oriented toward the inside of the cell, and further suggested a possible role in signal transduction. The N-terminal portion of the α subunit protein also possessed a hydrophobic amino acid sequence that was separated by two contiguous proline residues, an arrangement likely to induce a hairpin structure. This arrangement of two hydrophobic arms likely constitutes a putative fatty acid binding domain of the LSR. The α subunit also possessed a hydrophobic amino acid sequence consistent with a potential transmembrane domain (Brendel et al., *Proc. Natl. Acad. Sci. USA* 89:2002 (1992)). The β subunit protein does not possess a transmembrane domain and is probably positioned outside of the cell where it is bound through disulfide bridges to other components of the LSR complex.

Compositions and Methods for Modulating LSR Activity

An additional structural feature of the α and β subunit proteins related to the presence of repeated segments that were rich in serine and arginine residues. This was significant because the lamin receptor and "splicing factor 2" also have in common a repeated sequence of serine and arginine residues (RSRS), and these proteins also are known to combine with the gC1q-R protein (Honoré et al., *Gene* 134:283 (1993)). In view of t coincidence of related structural motifs and interactions with gC1q-R, we speculated that the serine and arginine rich segments of the LSR α and β subunits were somehow important for contact with gC1q-R, or the gC1q-R-like protein that was the γ subunit of the LSR complex.

As described in the following Example, polyclonal antibodies directed against synthetic peptides derived from the gC1q-R primary amino acid sequence were used to demonstrate that this protein, or a protein closely related to gC1q-R, was a component of the LSR complex. In the procedure described below, the anti-peptide antibodies inhibited the binding of labeled LDL to the LSR expressed on the surface of rat hepatocytes. Use of the LDL model substrate in these procedures provided a convenient and highly sensitive means for monitoring aspects of lipoprotein metabolism in liver cells.

Example 1 describes the procedures used to demonstrate that gC1q-R, or a closely related homologue of this protein, was a constituent of the LSR complex.

EXAMPLE 1

The gC1q-R or a gC1q-R-like Protein is a Component of the Multi-subunit LSR Rabbit polyclonal antibodies directed against two synthetic peptides having sequences located within the carboxy- and amino-terminal ends of the gC1q-R protein were prepared according to standard laboratory procedures. The synthetic peptide representing the N-terminal region of the protein had the sequence, LRCVPRVLGSSVAGY* (SEQ ID NO:3) and corresponded to residues 5–19 of the gC1q-R polypeptide sequence. The C-terminal synthetic peptide had the sequence, C*YITFLEDLKSFVKSQ (SEQ ID NO:4) and corresponded to residues 268–282 of gC1q-R. Amino acid positions marked with "*" indicate residues that differed from the wild type protein sequence in order to enhance peptide antigenicity. Peptides were coupled to a keyhole limpet hemocyacin (KLH) carrier prior to injection into rabbits. These procedures resulted in two serum samples, each with a binding specificity for a different region of the gC1q-R protein. Immunoglobulin G (IgG) from these sera were further purified using a Protein A column (Pharmacia) according to the manufacturer's instructions.

Increasing amounts of the these anti-peptide antibodies or an irrelevant IgG antibody were combined with $^{125}$I-LDL in a standard assay for measuring oleate-induced binding of LDL to plasma membranes of rat hepatocytes (Bihain et al., *Biochemistry* 31:4628 (1992); Mann et al., *J. Biol. Chem.* 272:31348 (1997)). The binding induced by oleate was determined as the difference between incubations with and without 0.5 mM oleate. Numerical measurements in this experiment were analyzed as the percent of total $^{125}$I-LDL bound to membranes in the absence of added antibodies.

The results presented in FIG. 1 indicated that antibodies directed to either of two regions of the gC1q-R protein inhibited LSR activity as measured by LDL binding. The negative control IgG did not inhibit LSR activity in this assay. This proved that inhibitory effects observed in our procedures were the results of specific antibody-receptor interactions. These results confirmed that gC1q-R, or a protein closely related to gC1q-R, was a component of the LSR complex.

The foregoing results seemingly suggested that agents which bound the gC1q-R, or the γ subunit of the LSR complex, had a negative or inhibitory effect on LSR activity. Thus, we had identified agents that were able to modulate LSR activity in a negative way.

In view of these findings, it was of interest to further evaluate the effects of compounds that bound to gC1q-R, or that might alter interactions between the γ subunit and the LSR. Since it was known that the C1q complement protein was a binding substrate for gC1q-R, we investigated whether C1q would modulate LSR activity in the same way that anti-peptide antibodies inhibited LSR activity in the preceding Example. Notably, the experiment described in the following Example was conducted both in the presence and absence of oleate, a free fatty acid that unmasks the lipoprotein binding site on the LSR.

Example 2 describes the procedures used to demonstrate that LSR activity could be modulated in a positive manner. Unexpectedly, enhancement of LSR activity took place both in the presence and absence of free fatty acids.

EXAMPLE 2

Regulation of LSR Activity by C1q and its Homologues

Primary cultures of rat hepatocytes were incubated with 20 ng of leptin/well using 6-well plates for 30 minutes at 37° C. in order to stimulate mobilization of LSR proteins to the cell surface and to increase the number of LSR receptors expressed. Increasing concentrations of C1q (Sigma) and 20 μg/ml of $^{125}$I-LDL were then added to parallel cell cultures in the presence or absence of 0.5 mM oleate. The mixtures were then incubated 4 hours at 37° C. and the binding, internalization and degradation of the labeled LDL analyzed using standard techniques (Bihain et al., *Biochemistry* 31:4628 (1992); Mann et al., *J. Biol. Chem.* 272:31348 (1997)).

Figures 2A, 2B, 2C:
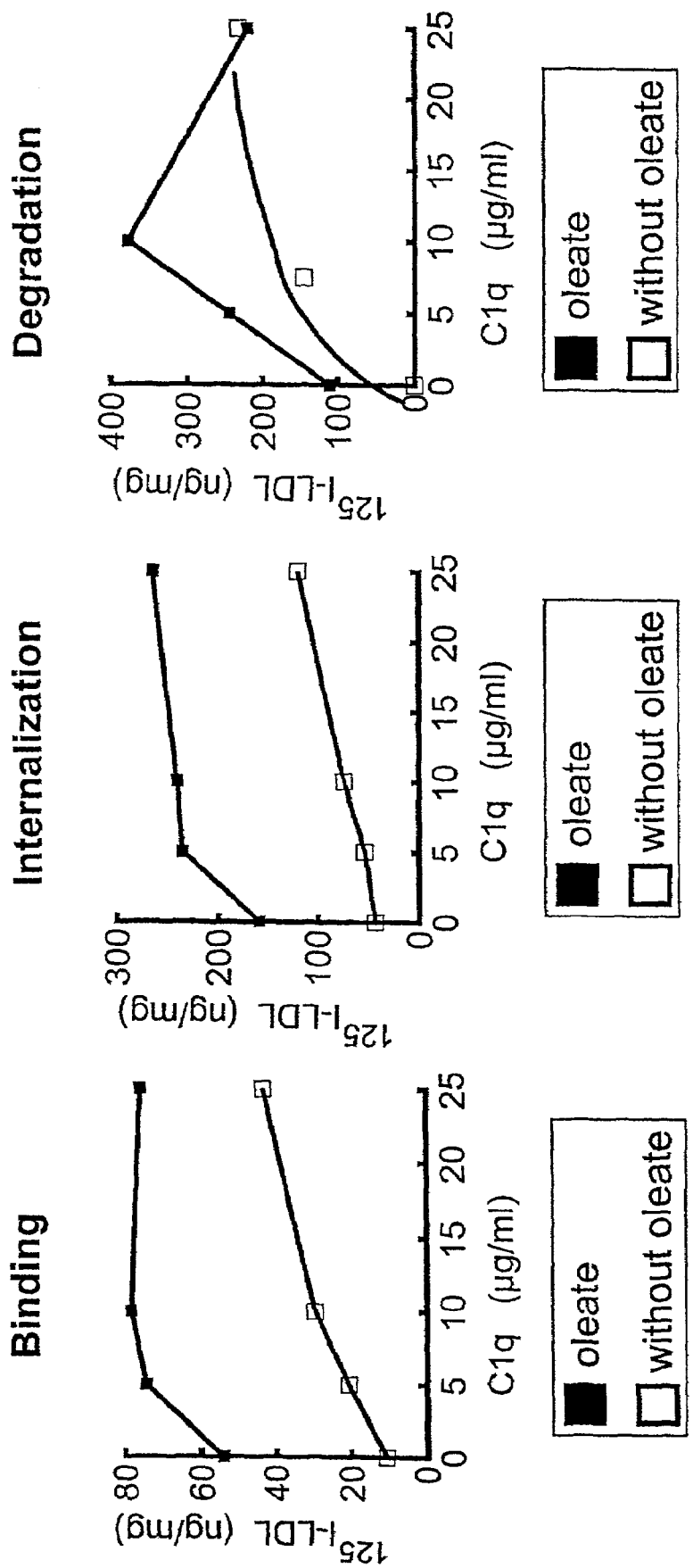
FIGS. 2A–2C show line graphs representing different aspects of LSR activity. The graphs show results for (A) binding, (B) internalization, and (C) degradation of labeled LDL, a model lipoprotein, in the presence and absence of oleate at increasing concentrations of C1q. Values on the vertical axis are presented in ng of $^{125}$I-LDL per mg of cellular protein that was bound, internalized and degraded per dish in the presence (■) or in the absence (□) of oleate.

The results presented in FIGS. 2A–C unexpectedly indicated that C1q enhanced LSR activity both in the presence and absence of free fatty acids. Indeed, it was surprizing that lipoprotein binding, internalization and degradation occurred in the absence of added aleate because these aspects of LSR activity were previously thought to require the presence of free fatty acids. Small but meaningful increases in all three of the measured parameters also were observed in the presence of oleate. The significance of these latter increases was less substantial because the background values measured in the absence of added C1q were higher in the presence of oleate compared to the values measured in the absence of this free fatty acid.

The results described in the preceeding Example showed that incubation of rat hepatocytes with C1q, a protein capable of binding gC1q-R and hence potentially capable of displacing it from the LSR complex, led to spontaneous activation of the LSR in the absence of free fatty acids. While not wishing to be bound by any particular theory which underlies the mechanism of this receptor modulation, we offer the following as a possible explanation for the phenomenon. It is possible that the gC1q-R protein, or more generally the γ subunit, functions as a chaperon protein for the LSR. It is further possible that the γ subunit somehow exerts an inhibitory effect on the LSR. Conceivably then, agents which perturb or alter the binding of the γ subunit to the LSR can be used to modulate LSR activity which can be measured in vitro as the binding, internalization and degradation of LDLs.

The exemplary case presented above suggested that C1q served as the agent that perturbed binding of the γ subunit in the LSR complex. However, we contemplate that any agent homologous or analogous to C1q that is able to bind gC2q-R or a gC1q-R-like protein also will have the effect of modulating LSR receptor activity.

The above-described effect of C1q on the activity of LSR led us to investigate whether similar effects on LSR would be promoted by proteins sharing structural homology with C1q. Alignments for some of these homologues are presented in FIG. 3, with the boxed regions representing conserved regions of structural homology. The murine proteins AdipoQ (Hu et al., *J. Biol. Chem.* 271:10697 (1996)) and Acrp30 (Scherer et al., *J. Biol. Chem.* 270:26746 (1995)), and the human ApM1 protein (Maeda et al., *Biochem. Biophys. Res. Commun.* 221:286 (1996)) clearly exhibit marked homologies. These three proteins, like the components of complement C1q (C1q A, B and C), are secreted proteins having N-terminal ends which resemble collagen (repetition of Gly-X-Y motifs), and C-terminal ends corresponding to the globular domain of complement C1q. Significantly, these three proteins are preferentially expressed in adipose tissue. Other protein homologues exhibit globular domains resembling the C1q domain. More specifically, cerebellin and multimerin (isolated in man), are two proteins that do not have a domain which resembles collagen.

Interestingly, conserved cysteine residues at positions 172, 179, 178 and 190, 196, 192 respectively in C1q A, C1q B and C1q C are not conserved in the other C1q homologues shown in the alignment. These cysteine residues are replaced in ApM1, AdipoQ and Acrp 30, by a lysine residue and an aspartate residue. Those having an ordinary level of skill in the art will appreciate that lysine and aspartate amino acids can, under appropriate conditions, form intrachain salt bridges which may contribute to protein structure. The amino acids at corresponding positions in cerebellin and multimerin would not allow for the formation of salt bridges. It is therefore possible to characterize the C1q domain of the proteins produced by the adipocytes by the absence of cysteines in the region corresponding to amino acids 170–200 of the molecules of C1q and by the consensus in the C1q domain.

When considering the structural relationship of the homologues presented in FIG. 3 it is worth noting that the protein ApM1, which is encoded by an mRNA characterized as being strongly expressed in adipocytes, exhibits 79.7% nucleic acid identity and 80.6% amino acid identity with AdipoQ. Given this level of sequence relatedness, the ApM1 protein is almost certainly the human homologue of murine AdipoQ. Thus, it is a reasonable expectation that the activities of murine AdipoQ which are disclosed below also will characterize ApM1 in a human system.

Given that C1q has a broad spectrum of biological effects, including initiation of the complement cascade, it seemed unlikely that the highly specialized activation of the LSR represented a physiologically significant function of this protein. Accordingly, we investigated whether C1q homologues could modulate LSR activity. As indicated in the Examples which follow, we have now demonstrated that AdipoQ, an abundant plasma protein having a heretofore unknown function, also enhances LSR activity.

AdipoQ is a C1q homologue that is known to be secreted by adipocytes with kinetics closely resembling to the kinetics of Adipsin secretion. Adipsin is a hormone of the complement system and has been shown to correspond to the purified fragment of the third component of complement, C3a-desArg (Baldo et al., *J. Clin. Invest.* 92:1543 (1993)). Adipsin stimulates adipocyte triglyceride synthesis and regulates postprandial lipemia (Sniderman et al., *Proc. Nutr. Soc.* 56:703 (1997)). Moreover, secretion of both AdipoQ and Adipsin is stimulated in response to insulin.

As supported by the experimental results presented below, we have proved that AdipoQ can stimulate LSR activity in vitro, and can decrease animal body weight. Since C1q and AdipoQ share structural homology without also sharing extensive functional similarities, our demonstration that AdipoQ activates LSR activity establishes the general utility of C1q homologues as compounds useful for modifying the activity of the LSR.

Example 3 describes the methods used to prepare an expression vector encoding murine Adipose

EXAMPLE 3

Construction of an Expression Vector Encoding Murine AdipoQ

Standard laboratory procedures were used to isolate RNA from adipose tissue that had been obtained from C57BL/6J mice. Poly(A)+mRNA was captured using oligo-dT coated magnetic beads according to the manufacturer's instructions (Dynal, France). The mRNA was reverse transcribed into cDNA using SUPERSCRIPT reverse transcriptase and reagents that were purchased as a kit (Life Technologies, France). cDNA encoding AdipoQ was amplified in a standard PCR protocol using oligonucleotide primers having the sequences: CTACATGGATCCAGTCATGCCGAAGAT (SEQ ID NO:5), and CGACAACTCGAGTCAGTTGG-TATCATGG (SEQ ID NO:6). This procedure selectively amplified polynucleotide sequences downstream of the putative signal sequence located at the 5' end of the AdipoQ coding region. The amplified cDNA was digested with BamHI and XhoI restriction endonucleases and the digestion products ligated into the corresponding sites of the pTRC His B expression vector (Invitrogen, France). This vector has been engineered to permit expression of heterologous sequences downstream of a polypeptide domain which includes a hexahistidine peptide motif, an enterokinase cleavage site and an epitope that is recognized by an ANTI-XPRESS antibody. Following transformation of competent DH5-α E. coli, bacterial clones harboring the polynucleotide encoding AdipoQ were selected by growth in the presence of ampicillin. Plasmid DNA was isolated from one of the bacterial clones and the sequence of the heterologous DNA insert determined. The sequence of the insert was found to correspond to bases 57–762 of AdipoQ (GeneBank accession No. U49915). The cloned polynucleotide sequence also corresponded to bases 86–791 of the sequence encoding Acrp30 (GeneBank accession No. U37222), except for nucleotide position 382. The polynucleotide sequence encoding Acrp 30 has an adenosine residue at this position while the AdipoQ polynucleotide has a guanine residue at the corresponding position. This nucleotide substitution leads to an amino acid change from a methionine in Acrp30 to a valine in AdipoQ.

With the availability of the above-described expression vector it became possible to produce recombinant AdipoQ protein that could be used to conduct experiments in vitro and in vivo.

Example 4 describes the procedures that were used to prepare a recombinant form of the AdipoQ protein.

EXAMPLE 4

Production and Purification of Recombinant AdipoQ Protein

Bacteria containing the AdipoQ expression vector were cultured at 37° C. in LB medium under antibiotic selection until the $OD_{600}$ reached 0.2. Production of recombinant protein was then induced by adding isopropyl-β-D thiogalactopyranoside to a final concentration of 1 mM. Bacterial growth proceeded for an additional 16 hours at 37° C., after which time the cultured bacteria were harvested by centrifugation. Bacteria were lysed according to standard laboratory procedures using lysozyme in a buffer that included Tris HCl (pH 7.4), NaCl, PMSF and sodium deoxycholate. DNA in the crude lysate was degraded by sonication. After centrifugation to remove cellular debris, the recombinant protein was isolated from the cleared supernatant using a PRO-BOND column (Invitrogen, France). The nickel-charged resin of the column has affinity for the above-described hexahistidine peptide motif of the recombinant fusion protein. Elution was achieved in the presence of imidazole. Following dialysis of the eluate, protein concentration was measured by the standard Lowry method. Purity of the recombinant protein was verified by SDS polyacrylamide gel electrophoresis. A single band of apparent molecular mass of about 33 kDa was observed on the protein gel. Notably, at this point the recombinant protein retained the hexahistidine protein domain.

We next employed an in vitro assay to investigate whether the recombinant AdipoQ, like C1q, stimulated LSR activity. Use of the in vitro assay allowed us to particularly study different aspects of LSR-mediated activity, including binding, internalization and degradation of a model lipoprotein substrate.

Example 5 describes the methods that were used to prove that AdipoQ stimulated LSR activity in vitro.

EXAMPLE 5

Recombinant AdipoQ Stimulates LSR Activity in Cultured Hepatocytes

Primary cultures of rat hepatocytes were prepared and plated in 6-well plates at 900,000 cells/well. After 48 hours the cells were washed once with 2 ml/well of phosphate buffered saline (PBS) and then incubated for 30 minutes at 37° C. with 20 ng/ml of recombinant murine leptin. Thereafter the cells were further incubated 4 hours at 37° C. with 25 µg/ml of recombinant AdipoQ and 20 µg/ml of $^{125}$I-LDL in the presence or absence of 0.6 mM oleate. Binding, internalization and degradation of the labeled LDL all were determined according to the above-referenced standard methods.

The results presented in FIGS. 4A–C show that AdipoQ significantly increased the amount of LDL that was bound, internalized and degraded by hepatocytes. Indeed, the results particularly indicated that degradation of LDL was dramatically enhanced by AdipoQ treatment of the hepatocytes. It is worth noting that in this setting the increase of LSR activity due to AdipoQ was measured in the presence of leptin. These results confirmed that AdipoQ was capable of increasing LSR activity in primary culture of rat hepatocytes.

Given the finding that AdipoQ dramatically enhanced LSR activity in vitro, it was of interest to determine whether the same pattern of activity would be repeated in vivo. This possibility was tested by feeding rats a high fat meal, administering the rats with recombinant AdipoQ, measuring plasma triglycerides and comparing the results with measurements taken in rats that did not receive AdipoQ. As described below, our findings indicated that administration with AdipoQ dramatically reduced the level of plasma triglycerides following the high-fat test meal.

Example 6 describes the procedures that were used to demonstrate that plasma triglyceride levels following a high-fat meal were reduced in animals that had been injected with AdipoQ.

EXAMPLE 6

AdipoQ Reduces Postprandial Blood Lipid Levels in vivo

Overnight-fasted male Sprague-Dawley rats (400–450 g) were gavaged with a high-fat test meal (time=0) and immediately administered by intravenous injection into the femoral vein with either 300 µl of PBS alone or containing 1 mg of recombinant murine AdipoQ. The test meal consisted of 60% fat (37% saturated, 27% mono-, and 36% polyunsaturated fatty acids), 20% protein and 20% carbohydrate, and provided 56 kcal of energy/kg of body weight. A second injection of AdipoQ was administered 2 hours after the test meal. Blood samples were taken at two hour intervals and plasma triglyceride levels were determined by a standard enzymatic assay using reagents that had been purchased as a kit (Boehringer Mannheim).

The results presented in FIG. 5 show that AdipoQ substantially decreased the magnitude of the postprandial triglyceride response. Quantitative values presented in the Figure represent the mean±standard deviation (n 3). Whereas the level of circulating triglycerides remained substantially constant in the animals administered with AdipoQ, the level increased in control animals until reaching a peak at about 4 hours. These in vivo results were consistent with the marked AdipoQ-dependent enhancement of LSR activity that we had observed in vitro.

Example 7 describes the procedures used to demonstrate that AdipoQ administration promoted weight loss and reduction of plasma triglyceride levels in normal animals. This was true even when the animals were placed on a high-fat diet. Notably, in this case the AdipoQ was administered by a slow infusion protocol instead of by injection.

EXAMPLE 7

Administration of AdipoQ by Infusion Stimulates Weight Loss and Reduction in Plasma Triglycerides Osmotic pumps (Alzet) were surgically inserted into the abdominal cavities of 12 male 400–450 g Sprague-Dawley rats. The pumps contained either 2 ml of PBS (pH 7.4) (control n=6) or 2 ml mouse recombinant AdipoQ (5 mg/ml PBS, n=6). The pumps used in this procedure were designed to deliver 10 μl/hour (50 μg AdipoQ/hour). Animals were weighed and then housed individually in metabolic cages. Three animals in each group were put either on regular chow diet or a high-fat diet ad libitum (day 0). The high-fat diet consisted of regular chow supplemented with 2% (w/v) cholesterol, 10% (w/v) saturated fat in the form of vegetaline, 10% (w/v) sunflower oil and 15% (w/v) sucrose. On day 3, the animals were weighed and blood samples were obtained from the tail vein. Plasma triglycerides were measured using an enzymatic kit.

The results presented in FIGS. 6A–B show that AdipoQ caused a significant reduction in plasma triglyceride levels in test animals fed either a regular or a high fat diet. Moreover, AdipoQ administration caused a reduction in body weight that was more pronounced in animals fed the high fat diet.

Example 8 describes the procedures that defined yet another effect of AdipoQ in vivo. More specifically, the results presented below demonstrate that test animals administered with AdipoQ unexpectedly reduced their food intake.

EXAMPLE 8

AdivoQ Administration Promotes Reduction of Food Intake in Genetically Obese Mice Both ob/ob and db/db mice housed in metabolic cages were injected daily for 5 days into the tail veins with either PBS alone or recombinant murine AdipoQ (100 μg) dispersed in a PBS carrier. The amount of food consumed daily by each animal was monitored for the period of the experiment.

The results presented in FIGS. 7A–B show that the average daily food intake of obese mice was significantly reduced after AdipoQ administration. The graphic data reflect the average food intake and standard deviation for 4 mice in each group, except for the db/db control group (n 3) in which one animal died before the end of the experiment. Significantly, the AdipoQ-dependent reduction in food intake was observed for the ob/ob and db/db groups of mice. This established that AdipoQ was useful for controlling food intake in the absence of leptin (ob/ob mice), and that AdipoQ was able to overcome the leptin resistance that is characteristic of db/db mice.

Example 9 describes a method that may be used to reduce plasma triglycerides and body mass in humans. While this exemplary case describes a treatment of obese humans, it is to be understood that non-obese humans may also be administered with the medicament described below. For purposes of procedures described in the following two Examples, a population of individuals with body mass index >35 is recruited and tested for diabetes (fasting plasma glucose levels >120 mg/dl) and hypertriglyceridemia or "HTG" (fasting triglyceride levels >150 mg/dl). Four groups of obese subjects are then constituted. These groups include: (1) subjects with obesity and no diabetes or HTG; (2) subjects with diabetes but no HTG; (3) subjects with HTG but no diabetes; and (4) subjects with diabetes and HTG.

EXAMPLE 9

Administration of a Medicament that Includes AdipoQ

A population of obese human individuals is first identified and then separated into two random groups. The control group receives a daily intravenous injection of a placebo for a period of from one week, two weeks, one month or more than a month. The placebo comprises a 1.0 ml volume of sterile PBS. Individuals in the treatment group receive an intravenous injection twice daily of a medicament that comprises 1.0 ml of sterile PBS containing recombinant AdipoQ at a dosage level corresponding to 2.5 mg AdipoQ/kg body mass. The recombinant AdipoQ is produced according to good manufacturing procedures (GMP) in a procaryotic expression system essentially according to the procedures described under Examples 3 and 4. Individuals in both groups consume high-fat meals, and serum triglyceride levels and body mass are monitored regularly for the duration of the procedure.

At the end of the treatment period it is clear that individuals administered with the medicament that included AdipoQ exhibit substantially reduced plasma triglyceride levels relative to the control group. Moreover, there is evidence that these individuals have experienced measurable weight reduction.

Example 10 describes how ApM1 can be used to stimulate reduction in plasma triglyceride levels and body mass.

EXAMPLE 10

ApM1 Administration Reduces Plasma Triglycerides and Body Mass

A population of obese human individuals is first identified and then separated into two random groups. The control group receives a daily intravenous injection of a placebo for a period of from one week, two weeks, one month or more than a month. The placebo comprises a 1.0 ml volume of sterile PBS. Individuals in the treatment group receive an intravenous injection twice daily of a medicament that comprises 1.0 ml of sterile PBS containing human ApM1 at a dosage level corresponding to 2.5 mg ApM1/kg body mass. The human ApM1 is a recombinant material produced according to GMP standards. For this purpose a procaryotic expression system is used essentially according to the procedures described under Examples 3 and 4, except that human ApM1 cDNA is substituted for the murine AdipoQ cDNA described in the Examples. Individuals in both groups consume high-fat meals. Serum triglyceride levels and body mass are monitored for both groups of individuals.

At the end of the treatment period individuals in the group administered with the medicament that included ApM1 exhibit substantially reduced plasma triglyceride levels relative to the control group. Moreover, these individuals have experienced measurable weight reduction.

Another aspect of the present invention relates to the preparation of a medicament for influencing the partitioning of dietary lipids between the adipose tissues and the liver in an individual. For example, the medicaments may increase or decrease the level of lipolysis which occurs in the liver. In particular, the medicaments may increase or decrease the level of lipolysis which occurs in the liver by increasing or decreasing the activity of LSR.

Such medicaments can be used in procedures for reducing the amount of dietary lipids stored in the adipose tissue or in procedures for increasing the amount of dietary lipids stored in the adipose tissue depending on the nature of the condition which is to be treated. In particular, such medicaments increase or decrease the activities of compounds (including AdipoQ, ApM1, C1q, any of the above-described compounds analogous to C1q, compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14) which increase the amount of dietary lipids partitioned to the liver.

Medicaments which increase the activity of these compounds in an individual may be used to reduce food intake in obese individuals, to reduce the levels of free fatty acids in obese individuals, to decrease the body weight of obese individuals, or to treat a variety of obesity related conditions. Such obesity related conditions include atherosclerosis (which may result from elevated levels of free fatty acids and chylomicron remnants in the plasma), obesity-related insulin resistance resulting from fatty acids in the plasma or fatty acids produced by extracellular lipolysis (Walker, M., Metabolism 44: 18–20 (1995); Lonnroth, P., Intern. Med. Suppl. 735: 23–29 (1991); Hannes, M. M. et al., Int. J. Obes. 14: 831–841 (1990), obesity-related hypertension resulting from fatty acids in the plasma or fatty acids produced by extracellular lipolysis (Goodfriend and Egan, J. Med. 344: 1649–1654 (1996), microangiopathic lesions resulting from obesity-related Type II diabetes, and ocular and renal lesions caused by microangiopathy in obese subjects with Type II diabetes.

Medicaments which decrease the activity of compounds which increase the partitioning of dietary lipids to the liver (including AdipoQ, ApM1, C1q, any of the above-described compounds analogous to C1q, compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14) may be used to treat conditions such as cachexia in subjects with neoplastic or para-neoplastic syndrome or eating disorders.

A variety of techniques may be used to increase the activity of compounds which increase the partitioning of dietary lipids to the liver. In particular, the activity of these compounds may be increased by directly administering these compounds (including AdipoQ, ApM1, C1q, any of the above-described compounds analogous to C1q, or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14 or a fragment of the preceding compounds) to the individual in any of the pharmaceutically acceptable formulations described above. Routes of administration of these compounds, as well as appropriate doses of these agents, have also been provided above.

Alternatively, the activity of compounds which increase the partitioning of dietary lipids to the liver may be increased by increasing the expression of the genes encoding these compounds using gene therapy. In such procedures, a nucleic acid encoding a compound, or a portion of a compound, which increases the partitioning of dietary lipids to the liver (including AdipoQ, ApM1, C1q, any of the above-described compounds analogous to C1q, derivatives of any of the preceding compounds, compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14 or a fragment of the preceding compounds) is transiently or stably introduced into the individual to be treated.

The nucleic acid encoding a compound, or a portion of a compound, which increases the partitioning of dietary lipids to the liver (including AdipoQ, ApM1, C1q, any of the above-described compounds analogous to C1q, or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14 or a fragment of the preceding compounds) is operably linked to a promoter capable of directing its expression. The promoter may be any of the promoters familiar to those of skill in the art including the Rous Sarcoma Virus promoter, the SV40 promoter, and the human cytomegalovirus promoter. In some embodiments, the promoter may be a liver-specific promoter. In further embodiments, the promoter may be the promoter from the LSR gene.

Additional vectors and promoters suitable for use in gene therapy include the parvovirus vectors disclosed in U.S. Pat. No. 5,252,479, the adenovirus vectors disclosed in U.S. Pat. No. 5,585,362, and the Harvey murine sarcoma virus vectors disclosed in U.S. Pat. No. 5,166,059. Other gene therapy vectors familiar to those of skill in the art may also be used, including moloney murine leukemia virus vectors, pLJ, pZIP, pWe and pEM.

Alternatively, the nucleic acid encoding a compound, or a portion of a compound, which increases the partitioning of dietary lipids to the liver (including AdipoQ, ApM1, C1q, any of the above-described compounds analogous to C1q, or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14 or a fragment of the preceding compounds) may be linked to a promoter capable of directing its expression and introduced into the individual as naked DNA using procedures such as those described in U.S. Pat. No. 5,558,059.

In further approaches, a nucleic acid encoding AdipoQ, ApM1, C1q, any of the above-described compounds analogous to C1q, a compounds having at least one consensus sequence selected from the group consisting of SEQ ID NO:1 and SEQ ID NO: 2, a compound comprising an amino acid sequence having at least 25% homology to a sequence selected from the group consisting of SEQ ID NOs. 7–14, a compound comprising an amino acid sequence having at least 50% homology to a sequence selected from the group consisting of SEQ ID NOs. 7–14, a compound comprising an amino acid sequence having at least 80% homology to a sequence selected from the group consisting of SEQ ID NOs. 7–14 or a fragment of any of the preceding compounds may be introduced into cells, such as fibroblast cells, using the gene therapy or naked DNA techniques described above. The cells, such as fibroblast cells, may be enclosed in a lattice of collagen and synthetic fibers coated with basic fibroblast growth factor so as to form an organoid. The organoid may then be transplanted into a host animal. Techniques for producing organoids are disclosed in Bohlet al., Gene Ther. 2:197–202 (1995) and Descampset al., Gene Ther. 2:411–417 (1995).

In another approach, the genes (or portions thereof) which encode compounds which increase the partitioning of dietary lipids to the liver (including AdipoQ, ApM1, C1q, any of the above-described compounds analogous to C1q, compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SED ID NOs. 7–14) may be mutagenized to create derivative proteins or peptides which have a greater ability to increase the partitioning of dietary lipids to the liver than the wild type proteins. A variety of mutagenesis procedures are known to those of skill in the art, including site directed mutagenesis and random chemical mutagenesis. For example, any of the mutagenesis procedures disclosed in Ausebel et al., Current Protocols in Molecular Biology, John Wiley & Sons (1998) may be used.

The proteins or peptides encoded by the mutagenized genes are inserted into expression vectors, isolated using techniques familiar to those skilled in the art, and tested to determine whether they have greater activity than the wild type proteins using the procedures described below.

Alternatively, rather than preparing derivatives using the mutagenesis procedures described above, combinatorial chemistry techniques which permit the generation of a large number of derivative peptides in vitro may be used.

Derivative proteins or peptides having increased activity relative to the wild type may be identified by comparing their activity to the activity of the wild type proteins or peptides in the rat hepatocyte assay of Example 5. Those derivative proteins or peptides which have increased activity relative to the wild type proteins may then be further analyzed in the postprandial lipemic response assay of Example 6, the plasma triglyceride assay of Example 7, the food intake assay of Example 8 or the weight loss assay of Example 7.

Those derivative proteins or peptides having increased activity relative to the wild type proteins may be used in medicaments to increase the partitioning of dietary lipids to the liver. In such medicaments, the derivative protein or peptide may be administered to the individual in a pharmaceutically acceptable carrier such as those described above. The derivative protein or peptide may be administered through any of the routes and at any of the dosages described above.

In addition, as discussed above, small molecules, drugs, or other compounds which increase the activity of a compound which increases the partitioning of dietary lipids to the liver may be obtained by using a variety of synthetic approaches familiar to those skilled in the art, including combinatorial chemistry based techniques. Candidate small molecules, drugs, or other compounds may be evaluated by determining their ability to increase the activity of a compound which increases the partitioning of dietary lipids to the liver in the rat hepatocyte assay of Example 5. Those compounds which increase the activity of a compound which increases the partitioning of dietary lipids to the liver in the rat hepatocyte assay may be further evaluated in the postprandial lipemic response assay of Example 6, the plasma triglyceride assay of Example 7, the food intake assay of Example 8, or the weight loss assay of Example 7.

As described above, the present invention also relates to medicaments for reducing the activity of compounds which increase the partitioning of dietary lipids to the liver. Such medicaments may be used to treat conditions such as those described above in which it is desirable to decrease the partitioning of dietary lipids to the liver (i.e. to increase the partitioning of dietary lipids to the adipose tissue). The activity of compounds which increase the partitioning of dietary lipids to the liver (including AdipoQ, ApM1, C1q, any of the above-described compounds analogous to C1q, or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14 or a fragment of the preceding compounds) may be reduced using a variety of methods, including the methods described below.

The partitioning of dietary lipids to the liver may also be increased by preparing an antibody which binds to the γ subunit, the C1q receptor (gC1q-R) or a protein related thereto, as well as fragments of these proteins. Such antibodies may modulate the interaction between LSR and the γ subunit, the C1q receptor (gC1q-R) or a protein related thereto in a manner which increases the partitioning of dietary lipids to the liver. The antibodies may be any of the antibodies described below.

In one procedure for reducing the activity of a compound which increases the partitioning of dietary lipids to the liver, an antibody which inhibits the activity of the compound is administered to an individual. The antibody may be polyclonal or monoclonal.

Polyclonal antibodies capable of specifically binding to a compound which increases the partitioning of dietary lipids to the liver may be obtained by using the compound (or a fragment thereof) as an immunogen in the procedures described in Example 1 above. Alternatively, polyclonal antibodies may be generated against the γ subunit, the C1q receptor (gC1q-R) or a protein related thereto, as well as fragments of these proteins.

Monoclonal antibodies to compounds which increase the partitioning of dietary lipids to the liver can be prepared from murine hybridomas according to the classical method of Kohler, G. and Milstein, C., Nature 256:495 (1975) or derivative methods thereof. Briefly, a mouse is repetitively inoculated with a few micrograms of the compound or a fragment thereof (such as AdipoQ, ApM1, C1q, any of the above-described compounds analogous to C1q, or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14 or a fragment of the preceding compounds) over a period of a few weeks. Alternatively, monoclonal antibodies may be generated against the γ subunit, the C1q receptor (gC1q-R) or a protein related thereto, as well as fragments of these proteins.

The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

Antibodies which are capable of inhibiting the activity of compounds which increase the partitioning of dietary lipids to the liver (including AdipoQ, ApM1, C1q, any of the above-described compounds analogous to C1q, compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14) may be identified by contacting the compound with increasing amounts of the monoclonal or polyclonal antibodies prior to conducting or while conducting the assay described in Example 5 with the compound. Those antibodies which reduce binding, internalization, and/or degradation in the rat hepatocyte assay may be tested for in vivo activity by administering increasing amounts of the antibodies to mice and determining the ability of the antibodies to inhibit the compound-mediated reduction in postprandial triglyceride response in the assay described in Example 6 above, the ability of the antibodies to inhibit the compound-mediated reduction in plasma triglycerides in the assay described in Example 7 above, the ability of the antibodies to inhibit the compound-mediated reduction of food intake in obese mice in the assay described in Example 8 above, or the ability of the antibodies to inhibit the compound-mediated weight loss in the assay described in Example 7.

The partitioning of dietary lipids to the liver may also be reduced by preparing an antibody which binds to the γ subunit, the C1q receptor (C1q-R) or a protein related thereto, as well as fragments of these proteins. Such antibodies may modulate the interaction between AdipoQ, ApM1, or analogous proteins and the γ subunit, the C1q receptor (gC1q-R) or a protein related thereto in a manner which reduces the partitioning of dietary lipids to the liver. The antibodies may be any of the antibodies described above.

Alternatively, the partitioning of dietary lipids to the liver may also be reduced using fragments of antibodies which retain the ability to specifically bind AdipoQ, ApM1, C1q, any of the above-described compounds analogous to C1q, compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, compounds comprising an amino acid sequence having at least 80% homology to a sequence selected from the group consisting of SEQ ID NOs. 7–14, the γ subunit, the C1q receptor (gC1q-R) or a protein related thereto, as well as fragments of these proteins. For example, the fragments may be Fab fragments, which may be prepared using methods familiar to those of skill in the art.

Alternatively, the antibodies may comprise humanized antibodies or single chain antibodies. A variety of methods for making humanized antibodies or single chain antibodies are familiar to those skilled in the art, including the techniques described in U.S. Pat. Nos. 5,705,154, 5,565332, and 5,608,039.

Those antibodies which inhibit the compound-mediated effects in one or more of the assays described above may then be used in medicaments for reducing the activity of compounds which increase the partitioning of dietary lipids to the liver. The antibodies may be administered to individuals in a pharmaceutically acceptable carrier such as those described above.

Alternatively, the activity of compounds which increase the partitioning of dietary lipids to the liver (including AdipoQ, ApM1, C1q, any of the above-described compounds analogous to C1q, or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14, or a fragment of the preceding compounds) may be reduced by reducing the expression of the genes encoding the compounds. A variety of approaches may be used to reduce gene expression, including antisense or triple helix based strategies.

In antisense approaches, nucleic acid sequences complementary to the mRNA encoding the compound capable of increasing the partitioning of dietary lipids to the liver are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribazyme capable of specifically cleaving the target mRNA.

The antisense nucleic acid molecules to be used in gene therapy may be either DNA or RNA sequences. They may comprise a sequence complementary to the sequence of a gene, or a portion of a gene, encoding a compound which increases the partitioning of dietary lipids to the liver. The antisense nucleic acids should have a length and melting temperature sufficient to permit formation of an intracellular duplex having sufficient stability to inhibit the expression of the mRNA in the duplex. Strategies for designing antisense nucleic acids suitable for use in gene therapy are disclosed in Green et al., Ann. Rev. Biochem. 55:569–597 (1986) and Izant and Weintraub, Cell 36:1007–1015 (1984), which are hereby incorporated by reference.

In some strategies, antisense molecules are obtained from a nucleotide sequence encoding a compound which increases the partitioning of dietary lipids to the liver by reversing the orientation of the coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of the antisense nucleic acids in vivo by operably linking DNA containing the antisense sequence to a promoter in an expression vector.

Alternatively, oligonucleotides which are complementary to the strand normally transcribed in the cell may be synthesized in vitro. For example, the oligonucleotides used in antisense procedures may be prepared on an oligonucleotide synthesizer or they may be purchased commercially from a company specializing in custom oligonucleotide synthesis, such as GENSET, Paris, France.

The antisense nucleic acids are complementary to the corresponding mRNA and are capable of hybridizing to the mRNA to create a duplex. In some embodiments, the antisense sequences may contain modified sugar phosphate backbones to increase stability and make them less sensitive to RNase activity. Examples of modifications suitable for use in antisense strategies are described by Rossi et al., Pharmacol. Ther. 50(2):245–254, (1991).

Various types of antisense oligonucleotides complementary to genes encoding compounds which influence the partitioning of dietary lipids to the liver (including genes encoding AdipoQ, ApM1, C1q, any of the above-described compounds analogous to C1q, compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, or compounds comprising an amino acid sequence having at least 80% homology to a sequence selected from the group consisting of SEQ ID NOs. 7–14) may be used. In one preferred embodiment, stable and semi-stable antisense oligonucleotides described in International Application No. PCT WO94/23026, hereby incorporated by reference, are used. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides described in International Application No. WO 95/04141, the disclosure of which is incorporated herein by reference, are used.

In yet another preferred embodiment, the covalently cross-linked antisense oligonucleotides described in International Application No. WO 96/31523, hereby incorporated by reference, are used. These double- or single-stranded oligonucleotides comprise one or more, respectively, inter- or intraoligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, hereby incorporated by reference are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, hereby incorporated by reference, is also contemplated. Because these molecules have no free ends, they are more resistant to degradation by exonucleases than are conventional oligonucleotides. These oligonucleotides may be multifunctional, interacting with several regions which are not adjacent to the target mRNA.

It is further contemplated that the antisense oligonucleotide sequence is incorporated into a ribozyme sequence to enable the antisense to specifically bind and cleave its target mRNA. For technical applications of ribozyme and antisense oligonucleotides see Rossi et al., supra.

The appropriate level of antisense nucleic acids required to inhibit gene expression may be determined using in vitro expression analysis. The antisense molecule may be introduced into cells which express the target gene by diffusion, injection, infection or transfection using procedures known in the art. For example, if the target gene is the AdipoQ gene or a gene encoding an analogous protein (such as the AdipoQ gene or the ApM1 gene), the antisense molecule may be introduced into adipocytes.

The antisense molecules are introduced onto cell samples at a number of different concentrations preferably between $1 \times 10^{-10}$M to $1 \times 10^{-4}$M. Once the minimum concentration that can adequately control gene expression is identified, the optimized dose is translated into a dosage suitable for use in vivo. For example, an inhibiting concentration in culture of $1 \times 10^{-7}$M translates into a dose of approximately 0.6 mg/kg bodyweight. Levels of oligonucleotide approaching 100 mg/kg body weight or higher may be possible after testing the toxicity of the oligonucleotide in laboratory animals.

When using the antisense molecules as a medicament, the antisense nucleic acids can be introduced into the body of an individual to be treated as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors such as those described above, vectors capable of extrachromosomal replication, or integrating vectors. The vectors may be DNA or RNA. It is additionally contemplated that cells from the vertebrate are removed, treated with the antisense oligonucleotide, and reintroduced into the vertebrate.

Alternatively, the activity of a compound which increases the partitioning of dietary lipids to the liver may be reduced using strategies based on intracellular triple helix formation. Triple helix oligonucleotides are used to inhibit transcription from a genome. They are particularly useful for studying alterations in cell activity as it is associated with a particular gene. The gene encoding a compound which increases the partitioning of dietary lipids to the liver (such as the gene encoding AdipoQ, ApM1, C1q, any of the above-described compounds analogous to C1q or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, or compounds comprising an amino acid sequence having at least 80% homology to a sequence selected from the group consisting of SEQ ID NOs. 7–14) or, more preferably, a portion of such a gene, can be used in triple helix based approaches to inhibit gene expression. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from genes encoding compounds which increase the partitioning of dietary lipids to the liver may be used in triple helix based approaches such as the following.

The sequence of a gene encoding a compound which increases the partitioning of dietary lipids to the liver is scanned to identify 10-mer to 20-mer homopyrimidine or homopurine stretches which could be used in triple-helix based strategies for inhibiting gene expression. In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (Science 245:967–971 (1989), which is hereby incorporated by this reference).

Following identification of candidate homopyrimidine or homopurine stretches, their efficiency in inhibiting gene expression may be assessed by introducing varying amounts of oligonucleotides containing the candidate sequences into cells which normally express the target gene and measuring the ability of the triple helix-forming nucleic acids to inhibit gene expression. For example, if the target gene is the AdipoQ gene or a gene encoding an analogous protein such as ApM1, the triple helix-forming nucleic acids may be introduced into adipocytes.

The oligonucleotides may be introduced into the cells using a variety of methods known to those skilled in the art, including but not limited to calcium phosphate precipitation, DEAE-Dextran, electroporation, liposome-mediated transfection or native uptake. Treated cells are monitored for reduced gene expression using techniques such as Northern blotting, RNase protection assays, or PCR based strategies to monitor the transcription levels of the target gene in cells which have been treated with the oligonucleotide.

The triple helix-forming oligonucleotides which are effective in inhibiting gene expression in tissue culture cells may then be used in medicaments for reducing the activity of the compound which increases the partitioning of dietary lipids to the liver. The triple helix-forming oligonucleotides may be introduced into an individual using the techniques provided in the above description of antisense strategies.

Alternatively, the activity of a compound which increases the partitioning of dietary lipids to the liver may be reduced using derivatives of the compound which inhibit its activity. For example derivatives of compounds which increase the partitioning of dietary lipids to the liver (such as derivatives of AdipoQ, ApM1, C1q, any of the above-described compounds analogous to C1q or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, compounds comprising an amino acid sequence having at least 80% homology to a sequence selected from the group consisting of SEQ ID NOs. 7–14, or fragments of any of these proteins) may be prepared using the mutagenesis or combinatorial chemistry procedures described above in connection with the preparation of derivatives having enhanced activity relative to the wild type.

Derivative proteins or peptides produced using the above procedures may be used in medicaments for reducing the activity of compounds which increase the partitioning of dietary lipids to the liver. Such mutant proteins or peptides may reduce the activity of a compound which increases the partitioning of dietary lipids to the liver (including AdipoQ, ApM1, C1q, any of the above-described compounds analogous to C1q, or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14) through a variety of mechanisms, including by acting as antagonists to binding of the wild type proteins to their ligands. For example, the antagonists may have a reduced activity and can thus reduce the activity of the compound by competing with it.

Derivative proteins or peptides which are capable of inhibiting the activity of the wild type protein may be identified by determining their ability to block the activity of the wild type proteins in assays such as the rat hepatocyte assay of Example 5, the postprandial lipemic response assay of Example 6, the plasma triglyceride assay of Example 7, the food intake assay of Example 8, or the weight loss assay of Example 7. Alternatively, the derivative proteins or peptides may be evaluated by determining their ability to increase food intake or cause a weight gain when administered in the assays of Examples 7 and 8.

Those derivative proteins or peptides which inhibit the activity of the wild type proteins may be used in medicaments for reducing the activity of a compound which increases the partitioning of dietary lipids to the liver. In such medicaments, the derivative protein or peptide may be administered to the individual in a pharmaceutically acceptable carrier such as those described above. The derivative protein or peptide may be administered through any of the routes and at any of the dosages described above.

In addition, as discussed above, small molecules, drugs, or other compounds which reduce the activity of a compound which increases the partitioning of dietary lipids to the liver may be obtained by using a variety of synthetic approaches familiar to those skilled in the art, including combinatorial chemistry based techniques. Candidate small molecules, drugs, or other compounds may be evaluated by determining their ability to inhibit the activity of a compound which increases the partitioning of dietary lipids to the liver in the rat hepatocyte assay of Example 5. Those compounds which inhibit the activity of a compound which increases the partitioning of dietary lipids to the liver in the rat hepatocyte assay may be further evaluated in the postprandial lipemic response assay of Example 6, the plasma triglyceride assay of Example 7, the food intake assay of Example 8, or the weight loss assay of Example 8.

Thus, one aspect of the present invention is an agent which increases the activity of a compound which increases the partitioning of dietary lipids to the liver for use as a pharmaceutical. In particular, the agent may be used for treating a condition selected from the group consisting of obesity, obesity-related atherosclerosis, obesity-related insulin resistance, obesity-related hypertension, obesity-related microangiopathic lesions, obesity-related ocular lesions, obesity-related renal lesions, and other conditions in which it is desirable to increase the partitioning of dietary lipids to the liver. In particular, the preceding conditions may be treated by administering a therapeutically effective amount of a compound which increases the partitioning of dietary lipids to the liver in a pharmaceutically acceptable carrier to an individual suffering from the preceding conditions. In some embodiments the redicament can be administered to an individual who has been determined to have less than the normal level of activity of a compound which increases the partitioning of dietary lipids to the liver. In particular, the medicament may comprise AdipoQ, ApM1, C1q, any of the above-described compounds analogous to C1q or compounds having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, compounds comprising an amino acid sequence having at least 80% homology to a sequence selected from the group consisting of SEQ ID NOs. 7–14, or fragments of any of these proteins.

Alternatively, the medicament may comprise a derivative of the preceding compounds which exhibits greater activity than the wild type compound or a nucleic acid which increases the level of expression of the preceding compounds in the individual.

Another aspect of the present invention is an agent which inhibits the activity of a compound which increases the partitioning of dietary lipids to the liver for use as a pharmaceutical. The pharmaceutical may be used for treating a condition selected from the group consisting of cachexia in subjects with neoplastic or para-neoplastic syndrome, eating disorders, and other conditions in which it is desirable to reduce the partitioning of dietary lipids to the liver. In particular, the preceding conditions may be treated by administering a therapeutically effective amount of an agent which inhibits the activity of a compound which increases the partitioning of dietary lipids to the liver in a pharmaceutically acceptable carrier to an individual suffering from the preceding conditions. In some embodiments the medicament can be administered to an individual who has been determined to have more than the normal level of activity of a compound which increases the partitioning of dietary lipids to the liver. In particular, the medicament may comprise an agent which inhibits the activity of AdipoQ, ApM1, C1q, any of the above-described compounds analogous to C1q, a compound having at least one consensus sequence selected from the group consisting of SEQ ID NO:1 and SEQ ID NO: 2, compounds comprising an amino acid sequence having at least 25% homology to a sequence selected from the group consisting of SEQ ID NOs. 7–14, compounds comprising an amino acid sequence having at least 50% homology to a sequence selected from the group consisting of SEQ ID NOs. 7–14, or a compound comprising an amino acid sequence having at least 80% homology to a sequence selected from the group consisting of SEQ ID NOs. 7–14. For example the medicament may comprise an antibody which inhibits the activity of AdipoQ, ApM1, C1q, any of the above-described compounds analogous to C1q, a compound having at least one consensus sequence selected from the group consisting of SEQ ID NO:1 and SEQ ID NO: 2, a compound comprising an amino acid sequence having at least 25% homology to a sequence selected from the group consisting of SEQ ID NOs. 7–14, a compound comprising an amino acid sequence having at least 50% homology to a sequence selected from the group consisting of SEQ ID NOs. 7–14, or a compound comprising an amino acid sequence having at least 80% homology to a sequence selected from the group consisting of SEQ ID NOs. 7–14. The medicament may also comprise a derivative of AdipoQ, ApM1, C1q, any of the above-described compounds analogous to C1q, a compounds having at least one consensus sequence selected from the group consisting of SEQ ID NO:1 and SEQ ID NO: 2, a compound comprising an amino acid sequence having at least 25% homology to a sequence selected from the group consisting of SEQ ID NOs. 7–14, a compound comprising an amino acid sequence having at least 50% homology to a sequence selected from the group consisting of SEQ ID NOs. 7–14, and compounds comprising an amino acid sequence having at least 80% homology to a sequence selected from the group consisting of SEQ ID NOs. 7–14, or a fragment of the preceding compounds which inhibits the activity of AdipoQ, ApM1, C1q, any of the above-described compounds analogous to C1q, a compound having at least one consensus sequence selected from the group consisting of SEQ ID NO:1 and SEQ ID NO: 2, a compound comprising an amino acid sequence having at least 25% homology to a sequence selected from the group consisting of SEQ ID NOs. 7–14, a compound comprising an amino acid sequence having at least 50% homology to a sequence selected from the group consisting of SEQ ID NOs. 7–14, or a compound comprising an amino acid sequence having at least 80% homology to a sequence selected from the group consisting of SEQ ID NOs. 7–14. Alternatively, the medicament may comprise a nucleic acid, such as an antisense nucleic acid or a triple helix-forming nucleic acid, which alters the expression or decreases the level of expression of AdipoQ, ApM1, C1q, any of the above-described compounds analogous to C1q, a compound having at least one consensus sequence selected from the group consisting of SEQ ID NO:1 and SEQ ID NO: 2, a compound comprising an amino acid sequence having at least 25% homology to a sequence selected from the group consisting of SEQ ID NOs. 7–14, a compound comprising an amino acid sequence having at least 50% homology to a sequence selected from the group consisting of SEQ ID NOs. 7–14, or a compound comprising an amino acid sequence having at least 80% homology to a sequence selected from the group consisting of SEQ ID NOs. 7–14 in the individual.

Obese individuals express lower than normal levels of AdipoQ or AdipoQ related compounds. (Hu et al., J. Biol. Chem. 271: 10697–10703 (1996)). Obese individuals having decreased activity of AdipoQ, ApM1, or analogous compounds in their plasma, body fluids, or body tissues may be at risk of developing a variety of conditions associated with partitioning lower than normal levels of dietary lipids to the liver (i.e. partitioning higher than normal levels of dietary lipids to the adipose tissues). In particular, such individuals may suffer from obesity-related atherosclerosis, obesity-related insulin resistance, obesity-related hypertension, obesity-related microangiopathic lesions, obesity-related ocular lesions, and obesity-related renal lesions. Accordingly, another aspect of the present invention is a method for determining whether an obese individual is at risk of suffering from a condition selected from the group consisting of obesity-related atherosclerosis, obesity-related insulin resistance, obesity-related hypertension, obesity-related microangiopathic lesions, obesity-related ocular lesions, obesity-related renal lesions comprising determining whether the individual has a below normal level of activity of AdipoQ, ApM1 or analogous compounds in plasma, body fluids, or body tissues.

The level of AdipoQ, ApM1 or analogous compounds in plasma, body fluids, or body tissues may be determined using a variety approaches. In particular, the level may be determined using ELISA, Western Blots, or protein electrophoresis.

Another aspect of the present invention relates to methods of identifying molecules which bind to the γ subunit. As discussed above, the γ subunit may be the C1q receptor (gC1q-R) or a protein related thereto. Accordingly, as used below, the terminology "γ subunit" will refer to gC1q-R or the related protein which makes up the γ subunit of the LSR complex.

Molecules which bind to the γ subunit may be used in the medicaments and methods of the present invention to increase or decrease the partitioning of dietary lipids to the liver. For example, such molecules may act as agonists or antagonists to stimulate or decrease the activity of LSR.

There are numerous methods available for identifying γ subunit ligands. One such method is described in U.S. Pat. No. 5,270,170, the disclosure of which is incorporated herein by reference. Briefly, in this method, a random peptide library is constructed. The random peptide library comprises a plurality of vectors encoding fusions between peptides to be tested for γ subunit binding activity and a DNA binding protein, such as the lac repressor encoded by the lacI gene. The vectors in the random peptide library also contain binding sites for the DNA binding protein, such as the lacO site in the case where the DNA binding protein is the lac repressor. The random peptide library is introduced into a host cell, where the fusion protein is expressed. The host cells are then lysed under conditions which permit the DNA binding portion of the fusion protein to bind to the DNA binding sites on the vector.

The vectors having the fusion proteins bound thereto are placed in contact with immobilized γ subunit, or an immobilized fragment of γ subunit under conditions which permit peptides to bind specifically. For example, γ subunit or a fragment thereof may be immobilized by affixing it to a surface such as a plastic plate or a particle. In particular, the immobilized fragment of γ subunit may comprise the C1q, AdipoQ or ApM1 binding site.

Those vectors which encode random peptides capable of binding to the immobilized γ subunit, or a fragment thereof, or the C1q, AdipoQ or ApM1 binding site thereof will be specifically retained on the surface via the interaction between the peptide and γ subunit, a fragment of the γ subunit, or the C1q, AdipoQ or ApM1 binding site thereof.

Alternatively, molecules capable of binding to the γ subunit may be identified using two-hybrid systems such as the MATCHMAKER Two Hybrid System 2 (Catalog No. K1604-1, Clontech). As described in the manual accompanying the MATCHMAKER Two Hybrid System 2 (Catalog No. K1604-1, Clontech), which is incorporated herein by reference, nucleic acids encoding the γ subunit, a fragment thereof, or a fragment comprising the C1q, AdipoQ or ApM1 binding site are inserted into an expression vector such that they are in frame with DNA encoding the DNA binding domain of the yeast transcriptional activator GAL4. Nucleic acids in a library which encode proteins or peptides which might interact with the γ subunit, a fragment of the γ subunit, or the C1q, AdipoQ or ApM1 binding site are inserted into a second expression vector such that they are in frame with DNA encoding the activation domain of CAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins or peptides which interact with the γ subunit, a fragment thereof, or the C1q, AdipoQ or ApM1 binding site.

Alternatively, to study the interaction of the γ subunit, a fragment thereof, or a fragment comprising the C1q, AdipoQ or ApM1 binding site thereof with drugs or small molecules, such as molecules generated through combinatorial chemistry approaches, the microdialysis coupled to HPLC method described by Wang et al., Chromatographia, 44, 205–208(1997) or the affinity capillary electrophoresis method described by Busch et al., J. Chromatogr. 777: 311–328 (1997), the disclosures of which are incorporated herein by reference can be used.

In further methods, proteins, peptides, drugs, small molecules, or other compounds which interact with the γ subunit, a fragment thereof, or a fragment comprising the C1q, AdipoQ or ApM1 binding site thereof may be identified using assays such as the following. The molecule to be tested for binding is labeled with a detectable label, such as a fluorescent, radioactive, or enzymatic tag and placed in contact with immobilized γ subunit, a fragment thereof, or a fragment comprising the C1q, AdipoQ or ApM1 binding site thereof under conditions which permit specific binding to occur. After removal of non-specifically bound molecules, bound molecules are detected using appropriate means.

Alternatively, proteins, peptides, drugs, small molecules, or other compounds which bind to γ subunit, a fragment thereof, or a fragment comprising the C1q, AdipoQ or ApM1 binding site thereof may be identified using competition experiments. In such assays, the γ subunit, a fragment thereof, or a fragment comprising the C1q, AdipoQ or ApM1 binding site thereof is immobilized to a surface, such as a plastic plate. Increasing amounts of the proteins, peptides, drugs, small molecules, or other compounds are placed in contact with the immobilized γ subunit, a fragment thereof, or a fragment comprising the C1q, AdipoQ or ApM1 binding site thereof in the presence of a detectably labeled known γ subunit ligand, such as AdipoQ, C1q, any of the above-described compounds analogous to C1q, a compound having at least one consensus sequence selected from the group consisting of SEQ ID NO:1 and SEQ ID NO: 2, a compound comprising an amino acid sequence having at least 25% homology to a sequence selected from the group consisting of SEQ ID NOs. 7–14, a compound comprising an amino acid sequence having at least 50% homology to a sequence selected from the group consisting of SEQ ID NOs. 7–14, or a compound comprising an amino acid sequence having at least 80% homology to a sequence selected from the group consisting of SEQ ID NOs. 7–14. For example, the γ subunit ligand may be detectably labeled with a fluorescent, radioactive, or enzymatic tag. The ability of the test molecule to bind the γ subunit, a fragment thereof, or a fragment comprising the C1q, AdipoQ or ApM1 binding site thereof is determined by measuring the amount of detectably labeled known ligand bound in the presence of the test molecule. A decrease in the amount of known ligand bound to the γ subunit, a fragment thereof, or a fragment comprising the C1q, AdipoQ or ApM1 binding site thereof when the test molecule is present indicates that the test molecule is able to bind to the γ subunit, a fragment thereof, or a fragment comprising the C1q, AdipoQ or ApM1 binding site thereof. This method may be used to identify compounds which bind to the γ subunit and which therefore represent potential agonists or antagonists of LSR activity which can be exploited in the medicaments described above.

Proteins, peptides, drugs, small molecules, or other compounds interacting with the γ subunit, a fragment thereof, or a fragment comprising the C1q, AdipoQ or ApM1 binding site thereof can also be screened by using an Optical Biosensor as described in Edwards et Leatherbarrow, Analytical Biochemistry, 246, 1–6 (1997), the disclosure of which is incorporated herein by reference. The main advantage of the method is that it allows the determination of the association rate between the γ subunit and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred manometers from the sensor surface). In these screening assays, the target molecule can be the γ subunit, a fragment thereof, or a fragment comprising the C1q, AdipoQ or ApM1 binding site thereof and the test sample can be a collection of proteins extracted from tissues or cells, a pool of expressed proteins, combinatorial peptide and/or chemical libraries, phage displayed peptides, drugs, small molecules or other compounds. The tissues or cells from which the test proteins are extracted can originate from any species.

Proteins or other molecules interacting with the γ subunit, a fragment thereof, or a fragment comprising the C1q, AdipoQ or ApM1 binding site thereof can be also be found using affinity columns which contain the γ subunit, a fragment thereof, or a fragment comprising the C1q, AdipoQ or ApM1 binding site thereof. The γ subunit, a fragment thereof, or a fragment comprising the C1q, AdipoQ or ApM1 binding site thereof may be attached to the column using conventional techniques including chemical coupling to a suitable column matrix such as agarose, Affi Gel, or other matrices familiar to those of skill in the art. In some versions of this method, the affinity column contains chimeric proteins in which the γ subunit, a fragment thereof, or a fragment comprising the C1q, AdipoQ or ApM1 binding site thereof is fused to glutathione S-transferase. A mixture of cellular proteins or pool of expressed proteins as described above and is applied to the affinity column. Proteins, peptides, drugs, small molecules or other molecules interacting with the γ subunit, a fragment thereof, or a fragment comprising the C1q, AdipoQ or ApM1 binding site thereof attached to the column can then be isolated and analyzed on 2-D electrophoresis gel as described in Ramunsen et al. Electrophoresis, 18, 588–598 (1997), the disclosure of which is incorporated herein by reference. Alternatively, the proteins or other molecules retained on the affinity column can be purified by electrophoresis based methods and sequenced. The same method can be used to isolate antibodies, to screen phage display products, or to screen phage display human antibodies.

The compounds identified using the above methods may be screened to determine whether they act as agonists or antagonists of LSR activity as follows. Those compounds which are agonists will increase LSR activity in one or more assays selected from the group consisting of the rat hepatocyte assay of Example 5, the postprandial lipemic response assay of Example 6, the plasma triglyceride assay of Example 7, the food intake assay of Example 8, or the body weight assay of Example 7. Such compounds are useful in the medicaments discussed above for treating conditions in which it is desirable to increase the partitioning of dietary lipids to the liver.

Alternatively, those compounds which are antagonists of LSR activity will inhibit the activity of AdipoQ in one or more assays selected from the group consisting of the rat hepatocyte assay of Example 5, the postprandial lipemic response assay of Example 6, the plasma triglyceride assay of Example 7, the food intake assay of Example 8, or the body weight assay of Example 7. Such compounds are useful in the medicaments discussed above for treating conditions in which it is desirable to reduce the partitioning of dietary lipids to the liver.

It will be appreciated that certain variations to this invention may suggest themselves to those skilled in the art. The foregoing detailed description is to be clearly understood as given by way of illustration, the spirit and scope of this invention being interpreted upon reference to the appended claims.

What is claimed is:

1. A method of increasing the partitioning of dietary lipids between the liver and peripheral tissues comprising the administration of an agent selected from adipose most abundant gene transcript 1 (ApM1), SEQ ID NO:11, or a biologically active homolog of ApM1 or SEQ ID NO: 11, said homolog having at least 80% homology to its respective sequence and the ability to increase partitioning of dietary lipids between the liver and peripheral tissues.

2. The method of claim 1, wherein said agent comprises ApM1.

3. The method of claim 1, wherein said agent comprises a fragment of ApM1.

4. The method of claim 1, wherein said agent comprises a biologically active homolog of SEQ ID NO:11.

5. The method according to claim 4, wherein said homolog exhibits at least one consensus sequence selected from SEQ ID NO:1 or SEQ ID NO:2.

6. The method of claim 1, wherein said agent comprises SEQ ID NO:11.

7. The method according to claim 1, wherein said administration comprises oral, rectal, transmucosal, intestinal, or parenteral administration of said agent.

8. The method according to claim 7, wherein said parenteral administration comprises intramuscular, subcutaneous, intramedullary, intravenous, intraperitoneal, or intranasal delivery.

9. The method according to claim 1, wherein said method further comprises surgical implantation of a device for the administration of said agent.

10. The method according to claim 1, wherein said agent consists of SEQ ID NO:11.

11. The method according to claim 1, wherein said agent consists of a homolog of SEQ ID NO: 11 having at least 80% homology to SEQ ID NO: 11 and the ability to increase partitioning of dietary lipids between the liver and peripheral tissues.

12. The method according to claim 11, wherein said homolog exhibits at least one consensus sequence selected from SEQ ID NO:1 or SEQ ID NO:2.

13. The method according to claim 1, wherein said homolog exhibits at least one consensus sequence selected from SEQ ID NO:1 or SEQ ID NO:2.

14. The method according to claim 1, wherein said agent is a biologically active homolog of ApM1.

15. The method according to claim 14, wherein said homolog exhibits at least one consensus sequence selected from SEQ ID NO:1 or SEQ ID NO:2.

16. A method of treating a condition in which it is desirable to increase the partitioning of dietary lipids to the liver, reduce the levels of free fatty acids in obese individuals, decrease the body weight of obese individuals, or treat an obesity related condition selected from the group consisting of obesity-related atherosclerosis, obesity-related insulin resistance, obesity-related hypertension, microangiopathic lesions resulting from obesity-related Type II diabetes, ocular lesions caused by microangiopathy in obese individuals with Type II diabetes, and renal lesions caused by microangiopathy in obese individuals with Type II diabetes comprising the administration of ApM1 or fragments of ApM1 wherein said fragments exhibit at least one consensus sequence slected from SEQ ID NO: 1 or SEQ ID NO: 2.

17. The method according to claim 16, wherein ApM1 is administered.

18. The method according to claim 16, wherein fragments of ApM1 are administered.

19. The method according to claim 18, wherein said fragment comprises SEQ ID NO:11.

* * * * *

UNITED STATES PATENT AND TRADEMARK OFFICE
CERTIFICATE OF CORRECTION

PATENT NO. : 7,220,722 B2
APPLICATION NO. : 10/072159
DATED : May 22, 2007
INVENTOR(S) : Bernard Bihain, Lydie Bougueleret and Frances Yen-Potin It is certified that error appears in the above-identified patent and that said Letters Patent is hereby corrected as shown below:

<u>Title Page, Item (54), and Col. 1, line 1</u>
Title, "Lipoprotein-Regulating Medicants" should read
--Lipoprotein-Regulating Medicaments--.

<u>Column 6,</u>
Line 9, "ApM" should read --ApM1--
Line 56, "SEQ ID MOs." should read --SEQ ID NOs.--.

<u>Column 9,</u>
Line 60, "that ran" should read --that can--.

<u>Column 13,</u>
Line 47, "intratheal" should read --intrathecal--.

<u>Column 16,</u>
Line 10, "dependent an" should read --dependent on--.

<u>Column 17,</u>
Line 10, "Acrp segment" should read -- Acrp 30 segment--.

<u>Column 21,</u>
Line 33, "of t coincidence" should read --of this coincidence--.

<u>Column 23,</u>
Line 36, "bind gC2q-R" should read --bind gC1q-R--.

<u>Column 24,</u>
Line 47, "Adipose" should read --AdipoQ.--.

<u>Column 27,</u>
Line 45, "AdivoQ" should read --AdipoQ--.

<u>Column 34,</u>
Line 29, "(C1q-R)" should read --(gC1q-R)--.

<u>Column 35,</u>
Line 33, "ribazyme" should read --ribozyme--.

UNITED STATES PATENT AND TRADEMARK OFFICE
CERTIFICATE OF CORRECTION

PATENT NO. : 7,220,722 B2
APPLICATION NO. : 10/072159
DATED : May 22, 2007
INVENTOR(S) : Bernard Bihain, Lydie Bougueleret and Frances Yen-Potin It is certified that error appears in the above-identified patent and that said Letters Patent is hereby corrected as shown below:

Column 42,
Line 67, "CAL4" should read --GAL4--.

Signed and Sealed this

Twenty-third Day of October, 2007

JON W. DUDAS
*Director of the United States Patent and Trademark Office*

SEQUENCE LISTING

```
<160> NUMBER OF SEQ ID NOS: 14

<210> SEQ ID NO 1
<211> LENGTH: 31
<212> TYPE: PRT
<213> ORGANISM: Homo sapiens
<220> FEATURE:
<221> NAME/KEY: VARIANT
<222> LOCATION: 2..6
<223> OTHER INFORMATION: Xaa=any amino acid
<221> NAME/KEY: VARIANT
<222> LOCATION: 7
<223> OTHER INFORMATION: Xaa=Asp or Asn
<221> NAME/KEY: VARIANT
<222> LOCATION: 8..11
<223> OTHER INFORMATION: Xaa=any amino acid
<221> NAME/KEY: VARIANT
<222> LOCATION: 12
<223> OTHER INFORMATION: Xaa=Phe or Tyr or Trp or Leu
<221> NAME/KEY: VARIANT
<222> LOCATION: 13..18
<223> OTHER INFORMATION: Xaa=any amino acid
<221> NAME/KEY: VARIANT
<222> LOCATION: 20..24
<223> OTHER INFORMATION: Xaa=any amino acid
<221> NAME/KEY: VARIANT
<222> LOCATION: 26
<223> OTHER INFORMATION: Xaa=any amino acid
<221> NAME/KEY: VARIANT
<222> LOCATION: 28
<223> OTHER INFORMATION: Xaa=any amino acid
<221> NAME/KEY: VARIANT
<222> LOCATION: 30
<223> OTHER INFORMATION: Xaa=any amino acid
<221> NAME/KEY: VARIANT
<222> LOCATION: 31
<223> OTHER INFORMATION: Xaa=Phe or Tyr

<400> SEQUENCE: 1

Phe Xaa Xaa Xaa Xaa Xaa Xaa Xaa Xaa Xaa Xaa Xaa Xaa Xaa Xaa Xaa
 1               5                  10                  15

Xaa Xaa Phe Xaa Xaa Xaa Xaa Xaa Gly Xaa Tyr Xaa Phe Xaa Xaa
            20                  25                  30

<210> SEQ ID NO 2
<211> LENGTH: 9
<212> TYPE: PRT
<213> ORGANISM: Homo sapiens
<220> FEATURE:
<221> NAME/KEY: VARIANT
<222> LOCATION: 1
<223> OTHER INFORMATION: Xaa=Ser or Thr
<221> NAME/KEY: VARIANT
<222> LOCATION: 2
<223> OTHER INFORMATION: Xaa=any amino acid
<221> NAME/KEY: VARIANT
<222> LOCATION: 4
<223> OTHER INFORMATION: Xaa=Ser or Thr
```

-continued

```
<221> NAME/KEY: VARIANT
<222> LOCATION: 6
<223> OTHER INFORMATION: Xaa=Phe or Tyr
<221> NAME/KEY: VARIANT
<222> LOCATION: 8
<223> OTHER INFORMATION: Xaa=Leu or Val
<221> NAME/KEY: VARIANT
<222> LOCATION: 9
<223> OTHER INFORMATION: Xaa=Phe or Tyr

<400> SEQUENCE: 2

Xaa Xaa Phe Xaa Gly Xaa Leu Xaa Xaa
1               5

<210> SEQ ID NO 3
<211> LENGTH: 15
<212> TYPE: PRT
<213> ORGANISM: Homo sapiens

<400> SEQUENCE: 3

Leu Arg Cys Val Pro Arg Val Leu Gly Ser Ser Val Ala Gly Tyr
1               5                   10                  15

<210> SEQ ID NO 4
<211> LENGTH: 16
<212> TYPE: PRT
<213> ORGANISM: Homo sapiens

<400> SEQUENCE: 4

Cys Tyr Ile Thr Phe Leu Glu Asp Leu Lys Ser Phe Val Lys Ser Gln
1               5                   10                  15

<210> SEQ ID NO 5
<211> LENGTH: 27
<212> TYPE: DNA
<213> ORGANISM: Homo sapiens
<220> FEATURE:
<221> NAME/KEY: misc_feature
<222> LOCATION: 12..27
<223> OTHER INFORMATION: identical to 58..73 in ref genbank U49915

<400> SEQUENCE: 5
ctacatggat ccagtcatgc cgaagat                                    27

<210> SEQ ID NO 6
<211> LENGTH: 28
<212> TYPE: DNA
<213> ORGANISM: Homo sapiens
<220> FEATURE:
<221> NAME/KEY: misc_feature
<222> LOCATION: 11..28
<223> OTHER INFORMATION: identical to 745..762 in ref genbank U49915
      (in complement)

<400> SEQUENCE: 6
cgacaactcg agtcagttgg tatcatgg                                   28

<210> SEQ ID NO 7
<211> LENGTH: 129
<212> TYPE: PRT
<213> ORGANISM: Homo sapiens
<220> FEATURE:
<221> NAME/KEY: SIMILAR
<222> LOCATION: 1..129
<223> OTHER INFORMATION: fragment 117..245 of ref swissprot P02745

<400> SEQUENCE: 7

Phe Ser Ala Ile Arg Arg Asn Pro Pro Met Gly Gly Asn Val Val Ile
```

```
                 1               5                  10                 15
Phe Asp Thr Val Ile Thr Asn Gln Glu Pro Tyr Gln Asn His Ser
                20                  25                  30

Gly Arg Phe Val Cys Thr Val Pro Gly Tyr Tyr Phe Thr Phe Gln
                35                  40                  45

Val Leu Ser Gln Trp Glu Ile Cys Leu Ser Ile Val Ser Ser Arg
                50                  55                  60

Gly Gln Val Arg Arg Ser Leu Gly Phe Cys Asp Thr Thr Asn Lys Gly
 65                 70                  75                  80

Leu Phe Gln Val Ser Gly Gly Met Val Leu Gln Leu Gln Gln Gly
                85                  90                  95

Asp Gln Val Trp Val Glu Lys Asp Pro Lys Lys Gly His Ile Tyr Gln
                100                 105                 110

Gly Ser Glu Ala Asp Ser Val Phe Ser Gly Phe Leu Ile Phe Pro Ser
                115                 120                 125

Ala

<210> SEQ ID NO 8
<211> LENGTH: 130
<212> TYPE: PRT
<213> ORGANISM: Homo sapiens
<220> FEATURE:
<221> NAME/KEY: SIMILAR
<222> LOCATION: 1..130
<223> OTHER INFORMATION: fragment 122..251 of ref swissprot P02745

<400> SEQUENCE: 8

Phe Ser Ala Thr Arg Thr Ile Asn Val Pro Leu Arg Arg Asp Gln Thr
 1               5                  10                  15

Ile Arg Phe Asp His Val Ile Thr Asn Met Asn Asn Asn Tyr Glu Pro
                20                  25                  30

Arg Ser Gly Lys Phe Thr Cys Lys Val Pro Gly Leu Tyr Tyr Phe Thr
                35                  40                  45

Tyr His Ala Ser Ser Arg Gly Asn Leu Cys Val Asn Leu Met Arg Gly
                50                  55                  60

Arg Glu Arg Ala Gln Lys Val Val Thr Phe Cys Asp Tyr Ala Tyr Asn
 65                 70                  75                  80

Thr Phe Gln Val Thr Thr Gly Gly Met Val Leu Lys Leu Glu Gln Gly
                85                  90                  95

Glu Asn Val Phe Leu Gln Ala Thr Asp Lys Asn Ser Leu Leu Gly Met
                100                 105                 110

Glu Gly Ala Asn Ser Ile Phe Ser Gly Phe Leu Leu Phe Pro Asp Met
                115                 120                 125

Glu Ala
    130

<210> SEQ ID NO 9
<211> LENGTH: 124
<212> TYPE: PRT
<213> ORGANISM: Homo sapiens
<220> FEATURE:
<221> NAME/KEY: SIMILAR
<222> LOCATION: 1..124
<223> OTHER INFORMATION: fragment 121..244 of ref swissprot P02745

<400> SEQUENCE: 9

Phe Thr Val Thr Arg Gln Thr His Gln Pro Pro Ala Pro Asn Ser Leu
 1               5                  10                  15
```

```
Ile Arg Phe Asn Ala Val Leu Thr Asn Pro Gln Gly Asp Tyr Asp Thr
            20                  25                  30

Ser Thr Gly Lys Phe Thr Cys Lys Val Pro Gly Leu Tyr Tyr Phe Val
        35                  40                  45

Tyr His Ala Ser His Thr Ala Asn Leu Cys Val Leu Leu Tyr Arg Ser
50                  55                  60

Gly Val Lys Val Val Thr Phe Cys Gly His Thr Ser Lys Thr Asn Gln
65                  70                  75                  80

Val Asn Ser Gly Gly Val Leu Leu Arg Leu Gln Val Gly Glu Glu Val
            85                  90                  95

Trp Leu Ala Val Asn Asp Tyr Tyr Asp Met Val Gly Ile Gln Gly Ser
            100                 105                 110

Asp Ser Val Phe Ser Gly Phe Leu Leu Phe Pro Asp
        115                 120
```

<210> SEQ ID NO 10
<211> LENGTH: 130
<212> TYPE: PRT
<213> ORGANISM: Homo sapiens
<220> FEATURE:
<221> NAME/KEY: SIMILAR
<222> LOCATION: 1..130
<223> OTHER INFORMATION: fragment 64..193 of translation from ref
      Genbank M58583

<400> SEQUENCE: 10

```
Phe Ser Ala Ile Arg Ser Thr Asn His Glu Pro Ser Glu Met Ser Asn
1               5                   10                  15

Arg Thr Met Ile Ile Tyr Phe Asp Gln Val Leu Val Asn Ile Gly Asn
            20                  25                  30

Asn Phe Asp Ser Glu Arg Ser Thr Phe Ile Ala Pro Arg Lys Gly Ile
        35                  40                  45

Tyr Ser Phe Asn Phe His Val Val Lys Val Tyr Asn Arg Gln Thr Ile
50                  55                  60

Gln Val Ser Leu Met Leu Asn Gly Trp Pro Val Ile Ser Ala Phe Ala
65                  70                  75                  80

Gly Asp Gln Asp Val Thr Arg Glu Ala Ala Ser Asn Gly Val Leu Ile
            85                  90                  95

Gln Met Glu Lys Gly Asp Arg Ala Tyr Leu Lys Leu Glu Arg Gly Asn
            100                 105                 110

Leu Met Gly Gly Trp Lys Tyr Ser Thr Phe Ser Gly Phe Leu Val Phe
        115                 120                 125

Pro Leu
    130
```

<210> SEQ ID NO 11
<211> LENGTH: 130
<212> TYPE: PRT
<213> ORGANISM: Homo sapiens
<220> FEATURE:
<221> NAME/KEY: SIMILAR
<222> LOCATION: 1..130
<223> OTHER INFORMATION: fragment 115..244 of translation from ref
      Genbank D45371

<400> SEQUENCE: 11

```
Phe Ser Val Gly Leu Glu Thr Tyr Val Thr Ile Pro Asn Met Pro Ile
1               5                   10                  15

Arg Phe Thr Lys Ile Phe Tyr Asn Gln Gln Asn His Tyr Asp Gly Ser
            20                  25                  30
```

```
Thr Gly Lys Phe His Cys Asn Ile Pro Gly Leu Tyr Tyr Phe Ala Tyr
            35                  40                  45

His Ile Thr Val Tyr Met Lys Asp Val Lys Val Ser Leu Phe Lys Lys
     50                  55                  60

Asp Lys Ala Met Leu Phe Thr Tyr Asp Gln Tyr Gln Glu Asn Asn Val
 65                  70                  75                  80

Asp Gln Ala Ser Gly Ser Val Leu Leu His Leu Glu Val Gly Asp Gln
                 85                  90                  95

Val Trp Leu Gln Val Tyr Gly Glu Gly Glu Arg Asn Gly Leu Tyr Ala
                100                 105                 110

Asp Asn Asp Asn Asp Ser Thr Phe Thr Gly Phe Leu Leu Tyr His Asp
            115                 120                 125

Thr Asn
    130

<210> SEQ ID NO 12
<211> LENGTH: 130
<212> TYPE: PRT
<213> ORGANISM: Mus musculus
<220> FEATURE:
<221> NAME/KEY: SIMILAR
<222> LOCATION: 1..130
<223> OTHER INFORMATION: fragment 118..247 of translation from ref
      Genbank U49915

<400> SEQUENCE: 12

Phe Ser Val Gly Leu Glu Thr Arg Val Thr Val Pro Asn Val Pro Ile
 1               5                  10                  15

Arg Phe Thr Lys Ile Phe Tyr Asn Gln Gln Asn His Tyr Asp Asn Ser
            20                  25                  30

Thr Gly Lys Phe Tyr Cys Asn Ile Pro Gly Leu Tyr Tyr Phe Ser Tyr
            35                  40                  45

His Ile Thr Val Tyr Met Lys Asp Val Lys Val Ser Leu Phe Lys Lys
     50                  55                  60

Asp Lys Ala Val Leu Phe Thr Tyr Asp Gln Tyr Gln Glu Lys Asn Val
 65                  70                  75                  80

Asp Gln Ala Ser Gly Ser Val Leu Leu His Leu Glu Val Gly Asp Gln
                 85                  90                  95

Val Trp Leu Gln Val Tyr Gly Asp Gly Asp His Asn Gly Leu Tyr Ala
                100                 105                 110

Asp Asn Val Asn Asp Ser Thr Phe Thr Gly Phe Leu Leu Phe His Asp
            115                 120                 125

Thr Asn
    130

<210> SEQ ID NO 13
<211> LENGTH: 130
<212> TYPE: PRT
<213> ORGANISM: Mus musculus
<220> FEATURE:
<221> NAME/KEY: SIMILAR
<222> LOCATION: 1..130
<223> OTHER INFORMATION: fragment 118..267 of translation from ref
      genbank U37222

<400> SEQUENCE: 13

Phe Ser Val Gly Leu Glu Thr Arg Val Thr Val Pro Asn Val Pro Ile
 1               5                  10                  15

Arg Phe Thr Lys Ile Phe Tyr Asn Gln Gln Asn His Tyr Asp Gly Ser
```

-continued

```
              20                  25                  30
Thr Gly Lys Phe Tyr Cys Asn Ile Pro Gly Leu Tyr Tyr Phe Ser Tyr
            35                  40                  45

His Ile Thr Val Tyr Met Lys Asp Val Lys Val Ser Leu Phe Lys Lys
     50                  55                  60

Asp Lys Ala Val Leu Phe Thr Tyr Asp Gln Tyr Gln Glu Lys Asn Val
 65              70                  75                  80

Asp Gln Ala Ser Gly Ser Val Leu Leu His Leu Glu Val Gly Asp Gln
                 85                  90                  95

Val Trp Leu Gln Val Tyr Gly Asp Gly Asp His Asn Gly Leu Tyr Ala
            100                 105                 110

Asp Asn Val Asn Asp Ser Thr Phe Thr Gly Phe Leu Leu Tyr His Asp
            115                 120                 125

Thr Asn
    130

<210> SEQ ID NO 14
<211> LENGTH: 126
<212> TYPE: PRT
<213> ORGANISM: Homo sapiens
<220> FEATURE:
<221> NAME/KEY: SIMILAR
<222> LOCATION: 1..126
<223> OTHER INFORMATION: fragment 1161..1286 of translation from ref
      genbank:U27109

<400> SEQUENCE: 14

Phe Phe Ala Ser His Thr Tyr Gly Met Thr Ile Pro Gly Pro Ile Leu
 1               5                  10                  15

Phe Asn Asn Leu Asp Val Asn Tyr Gly Ala Ser Tyr Thr Pro Arg Thr
            20                  25                  30

Gly Lys Phe Arg Ile Pro Tyr Leu Gly Val Tyr Val Phe Lys Tyr Thr
            35                  40                  45

Ile Glu Ser Phe Ser Ala His Ile Ser Gly Phe Leu Val Val Asp Gly
     50                  55                  60

Ile Asp Lys Leu Ala Phe Glu Ser Glu Asn Ile Asn Ser Glu Ile His
 65              70                  75                  80

Cys Asp Arg Val Leu Thr Gly Asp Ala Leu Leu Glu Leu Asn Tyr Gly
                 85                  90                  95

Gln Glu Val Trp Leu Arg Leu Ala Lys Gly Thr Ile Pro Ala Lys Phe
            100                 105                 110

Pro Pro Val Thr Thr Phe Ser Gly Tyr Leu Leu Tyr Arg Thr
            115                 120                 125
```